US009750806B2

(12) United States Patent
Lindhofer

(10) Patent No.: US 9,750,806 B2
(45) Date of Patent: Sep. 5, 2017

(54) VACCINE PREPARATION CONTAINING TRIFUNCTIONAL ANTIBODIES WITH ANTIGEN IMMUNOGENICITY ENHANCER PROPERTIES

(75) Inventor: Horst Lindhofer, Munich (DE)

(73) Assignee: Trion Research GmbH, Munich (DE)

( * ) Notice: Subject to any disclaimer, the term of this patent is extended or adjusted under 35 U.S.C. 154(b) by 546 days.

(21) Appl. No.: 14/118,212

(22) PCT Filed: May 16, 2012

(86) PCT No.: PCT/EP2012/059079
§ 371 (c)(1),
(2), (4) Date: May 15, 2014

(87) PCT Pub. No.: WO2012/156430
PCT Pub. Date: Nov. 22, 2012

(65) Prior Publication Data
US 2014/0286999 A1 Sep. 25, 2014

(30) Foreign Application Priority Data

May 17, 2011 (EP) .................................. 11166386
Mar. 6, 2012 (EP) .................................. 12158164

(51) Int. Cl.
| *A61K 39/00* | (2006.01) |
| *A61K 39/002* | (2006.01) |
| *A61K 39/02* | (2006.01) |
| *A61K 39/12* | (2006.01) |
| *A61K 39/385* | (2006.01) |
| *A61K 39/395* | (2006.01) |
| *A61K 39/40* | (2006.01) |
| *A61K 39/42* | (2006.01) |
| *C07K 16/28* | (2006.01) |
| *C07K 16/30* | (2006.01) |
| *C07K 16/46* | (2006.01) |

(52) U.S. Cl.
CPC ...... *A61K 39/3955* (2013.01); *A61K 39/0005* (2013.01); *A61K 39/385* (2013.01); *C07K 16/283* (2013.01); *C07K 16/30* (2013.01); *C07K 16/468* (2013.01); *A61K 2039/505* (2013.01); *A61K 2300/00* (2013.01); *C07K 2317/24* (2013.01); *C07K 2317/31* (2013.01); *C07K 2317/732* (2013.01)

(58) Field of Classification Search
None
See application file for complete search history.

(56) References Cited

U.S. PATENT DOCUMENTS

| 6,258,358 B1 * | 7/2001 | Romet-Lemonne ........... A61K 47/48369 424/134.1 |
| 6,994,853 B1 * | 2/2006 | Lindhofer .......... A61K 39/0011 424/130.1 |
| 2006/0115481 A1 | 6/2006 | Lindhofer et al. |

FOREIGN PATENT DOCUMENTS

| EP | 0245078 A2 | 11/1987 |
| EP | 0885614 A2 | 12/1998 |
| EP | 1666500 A1 | 6/2006 |
| WO | 0018435 A1 | 4/2000 |

OTHER PUBLICATIONS

Brady, "Antibody-Mediated Immunomodulation: a Strategy to Improve Host Responses against Microbial Antigens," *Infection and Immunity*, vol. 73(2), pp. 671-678 (2005).
Chelius, et al., Structural and functional characterization of the trifunctional antibody catumaxomab, MABS, Landes Bioscience, vol. 2(3), pp. 309-319 (2010).
Kim, et al., Antibody association with HER-2/neu-targeted vaccine enhances $CD8^+T$ cell responses in mice through Fc-mediated activation of DCs, *The Journal of Clinical Investigation*, vol. 118(5), pp. 1700-1711 (2008).
Mocikat, et al., "Trioma-based Vaccination against B-Cell Lymphoma Confers Long-Lasting Tumor Immunity," *Cancer Research*, vol. 57(12), pp. 2346-2349 (1997).
Morecki, et al., Induction of long-lasting antitumor immunity by concomitant cell therapy with allogeneic lymphocytes and trifunctional bispecific antibody, *Experimental Hematology*, vol. 6(8), pp. 997-1003 (2008).
Ruf, et al., "Induction of a long-lasting antitumor immunity by a trifunctional bispecific antibody," *Blood*, vol. 98(8), pp. 2526-2534 (2001).
Snider, "Immunization With Antigen Bound to Bispecific Antibody Induces Antibody That is Restricted in Epitope Specificity and Contains Antiidiotype," *Journal of Immunology*, vol. 148(4), pp. 1163-1170 (1992).
Snider, et al., "Enhanced Antigen Immunogenicity Induced by Specific Antibodies," *The Journal of Experimental Medicine*, vol. 171(6), pp. 1957-1963 (1990).
Tiong, et al., "Comparison of conventional adjuvants and 'adjuvant-free' monoclonal antibody targeting for stimulating antibody responses against a conjugate of luteinizing hormone releasing hormone and avidin," *Vaccine*, vol. 11(4), pp. 425-430 (1993).

(Continued)

*Primary Examiner* — Karen Canella
(74) *Attorney, Agent, or Firm* — Kilpatrick Townsend & Stockton LLP

(57) ABSTRACT

The present invention refers to a pharmaceutical composition containing trifunctional bispecific and/or trispecific antibodies being capable of binding to a specific target antigen(s) for use in a method of immunizing mammals against diseases in which said target antigen(s) is (are) involved, and further to a pharmaceutical composition containing trifunctional bispecific and/or trispecific antibodies being capable of binding to (a) specific target antigen (s) which is (are) involved in a disease of a mammal, specifically a human.

23 Claims, 13 Drawing Sheets

(56) References Cited

OTHER PUBLICATIONS

Wolpoe, et al., "HER-2/neu-Specific Monoclonal Antibodies Collaborate with HER-2/neu-Targeted Granulocyte Macrophage Colony-Stimulating Factor Secreting Whole Cell Vaccination to Augment CD8$^+$T Cell Effector Function and Tumor-Free Survival in HER-2/neu-Transgenic Mice1," *Journal of Immunology*, vol. 171(4), pp. 2161-2169 (2003).

Ströhlein, et al., "Induction of anti-tumor immunity by trifunctional antibodies in patients with peritoneal carcinomatosis," *Journal of Experimental and Clinical Cancer Research*, vol. 28(1), 10 pages (2009).

International Search Report for PCT/EP2012/059079, 6 pages, mailed Jul. 11, 2012.

\* cited by examiner

VACCINE PREPARATION CONTAINING TRIFUNCTIONAL ANTIBODIES WITH ANTIGEN IMMUNOGENICITY ENHANCER PROPERTIES

CROSS-REFERENCE TO RELATED APPLICATIONS

This application is the U.S. National Stage entry of PCT/EP2012/059079, filed May 16, 2012, which claims priority to European Application No. 11166386.0, filed May 17, 2011, and European Application No. 12158164.9, filed Mar. 6, 2012, which are incorporated in their entirety herein.

The present invention refers to a pharmaceutical composition containing trifunctional bispecific and/or trispecific antibodies being capable of binding to a specific target antigen(s) for use in a method of immunizing mammals against diseases in which said target antigen(s) is (are) involved, and further to a pharmaceutical composition containing trifunctional bispecific and/or trispecific antibodies being capable of binding to (a) specific target antigen (s) which is (are) involved in a disease of a mammal, specifically a human.

INTRODUCTION

Trifunctional bispecific and trispecific antibodies binding (i) to the T cell receptor complex of a T cell, (ii) to the surface-exposed tumor-associated antigen on a tumor cell and to the activating Fc-gamma receptor I, II or III on an accessory cell (i.e. natural killer cell, macrophage, monocyte, dendritic cell) have been described in U.S. Pat. No. 6,551,592 as having the capacity to induce anti-tumor immunity. The anti-tumor immunity is generated by administering an efficient amount of an trifunctional intact bispecific and/or trispecific antibody having the following properties and effects of: (a) binding to a T cell and mediating a first activation signal thereto; (b) binding to tumor-associated antigens on a tumor cell; (c) binding, through its Fc portion (in the case of trifunctional bispecific antibodies) or a third specificity (in the case of trispecific antibodies) to the Fc-gamma receptor of Fc-gamma receptor-positive cells; (d) activation of the Fc receptor-positive cell by binding to the Fc-gamma receptor-positive cell and, thereby initiating or increasing the expression of cytokines and/or co-stimulatory antigens; (e) transfer of at least one second activation signal required for physiological activation of the T cell to the T cell by the co-stimulatory antigens and/or cytokines, wherein said activation causes an up-regulation of activation markers, killing of the tumor cell, and/or T cell proliferation. According to an example of U.S. Pat. No. 6,551,592, C57BL/6 mice were first injected with $5 \times 10^3$ syngeneic B16 tumor cells. Two days later, one group of mice (n=18) was treated with a trifunctional bispecific antibody.

Hence the trifunctional antibodies had been applied separately from the tumor cells, and there is no disclosure of applying tumor antigens together with trifunctional antibodies. U.S. Pat. No. 7,018,632 B2 also describes ex vivo incubation of inactivated tumor cells with trifunctional bispecific antibodies. This is indeed the conventional approach using complete cells for the induction of an anti-tumor immunity.

It is obvious that this approach might have the disadvantage that not all of the tumor cells are inactivated or that any other infectious or harmful components of the tumor cell are administered into the patient's body. Moreover, the handling of tumor cells under GMP conditions is much more complicated than using proteins.

Snider et al. (1990) describe that the targeting of an antigen to professional antigen-presenting cell (APC) surfaces by heterocrosslinked bispecific antibodies greatly increase the efficiency with which APC endocytose, process, and present an antigen. Since antibody responses against most protein antigens require T cell help in vivo, Snider et al. (1990) have asked if heterocrosslinked bispecific antibodies could also enhance the ability of an antigen to induce an antibody response in mice. Normally, the generation of immune responses after immunization with vaccines and other antigens requires relatively large amounts of antigen, multiple injections, and, in experimental animals, adjuvants.

By contrast, Snider et al. (1990) showed that heterocrosslinked bispecific antibodies (anti-hen-egg-lysozymex anti-MHC II), induce high titers of antibodies in mice when administered once with nanogram amounts of xenogeneic antigen, in the absence of an adjuvant and prime mice for a secondary IgG antibody response when re-challenged with soluble antigen. It is of particular importance that Snider et al. do not provide any evidence of a T cell response in their experiments. Generating a T cell response by the antibodies used by Snider et al. is not only highly unlikely but even excluded as the Fc-part of conventional antibodies does not generate a T cell response on its own but necessitates the external addition of cytokines in order to generate a proper CD8 T cell response (e.g. IL-2, [Thibault et al., Int. J. Cancer 67(2): 232, 1996]) which is not necessary when the antibodies of the invention are used). Of note, the report by Snider et al. (1990) did not describe the induction of CD8 T cell responses in vivo that clearly required intact antibodies for an experimental tumor therapy. Exemplarily, CD8 T cell responses and anti-tumor protection are strongly induced by whole cell vaccine immunization in combination with a conventional IgG-like shaped antibody (with a functional Fc region) simultaneously recognizing a surface-exposed target antigen and Fc-receptors (Kim et al., 2008). It should be noted that both antibody entities used by Kim et al. (2008) and Snider et al. (1990) did only trigger enhanced Fc-receptor- or MHC class II-mediated antigen uptake by accessory cells without the involvement of T cells, respectively, leading to the improved immunization outcome.

In contrast, trifunctional bispecific and trispecific antibodies mediate immunization effects by binding simultaneously to T cells via anti-CD3 recognition and to accessory cells via Fc-gamma-receptor engagement. Thus, compared to Kim et al. (2008) and Snider et al. (1990) only trifunctional bispecific and trispecific antibodies are capable to trigger T cells directly for evoking a certain cytokine milieu and co-stimulation signals that in turn allow immunization in context of whole cell vaccines and as here demonstrated even against soluble antigen entities. It should be noticed that trifunctional (e.g. a murine IgG2a half antibody/rat IgG2b half antibody) or trispecific antibodies require the interaction between Fc-region and activating Fc-gamma-receptors on antigen-presenting cells (APC) for the priming of humoral and cell-mediated immune responses against cell-associated and, as here demonstrated, even soluble target antigens.

Starting with this prior art, it is a problem of the present invention to provide an improved vaccination method and a pharmaceutical preparation for immunizing a mammal to raise a humoral and/or cellular immune response against (a) target antigen(s) which is (are) involved in diseases of said mammals which are able to be prevented or cured (i.e. therapeutic vaccination) or alleviated by a vaccine treatment.

This problem is solved by the invention as described in the enclosed independent claims. Preferred embodiments of the invention are included in the dependent claims and are further described in the present description, the examples and the figures and tables.

Bars represent mean values of quadruplicate determinations with SD (error bars). Asterisk indicates statistically significant difference of spot numbers in comparison to naïve control and VLP-EpCAM immunization group (two-tailed, unpaired t-test, p=0.0362, respectively p=0.0089). A cell pool of each three mice per immunization group was analyzed.

Figure 7A:
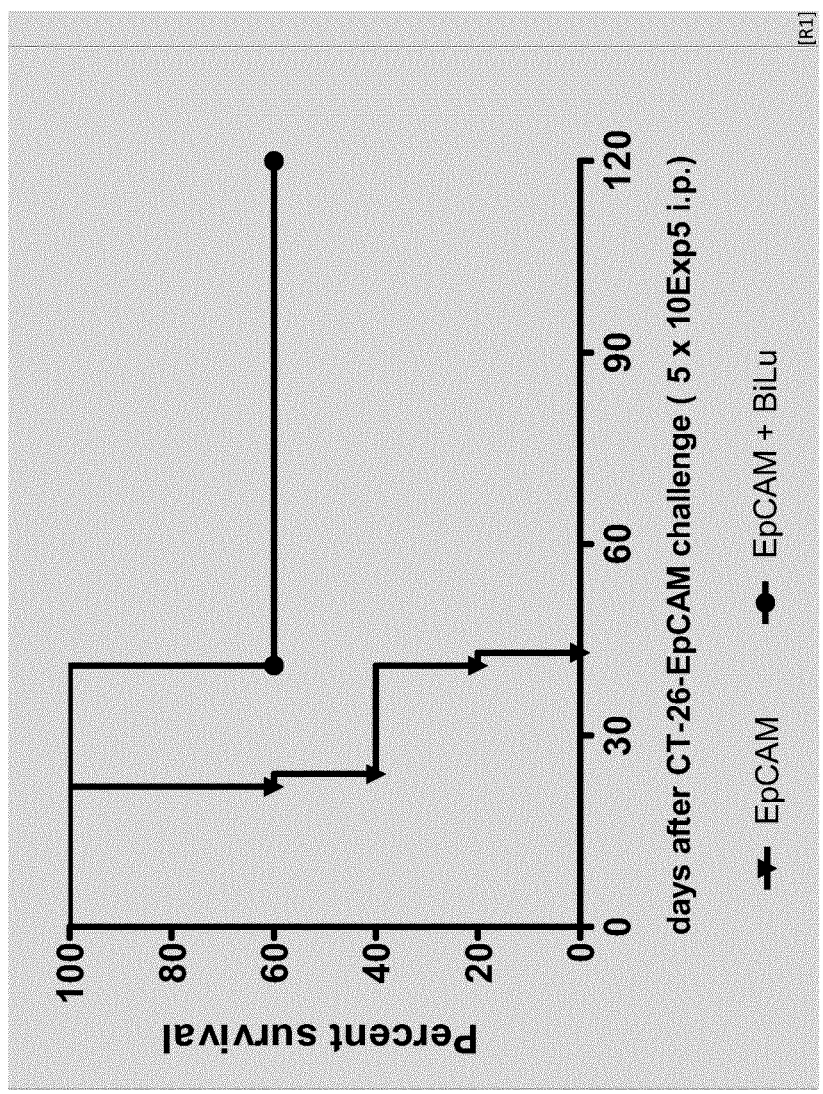

FIG. 7A: Survival of mice—immunization groups EpCAM vs. EpCAM+BiLu

Immunization group EpCAM+BiLu (n=5) shows significant prolonged survival in comparison to mice immunized with EpCAM protein only (n=5) after a lethal tumor challenge with CT26-EpCAM tumor cells (log-rank test, p=0.0257)

Figure 7B:
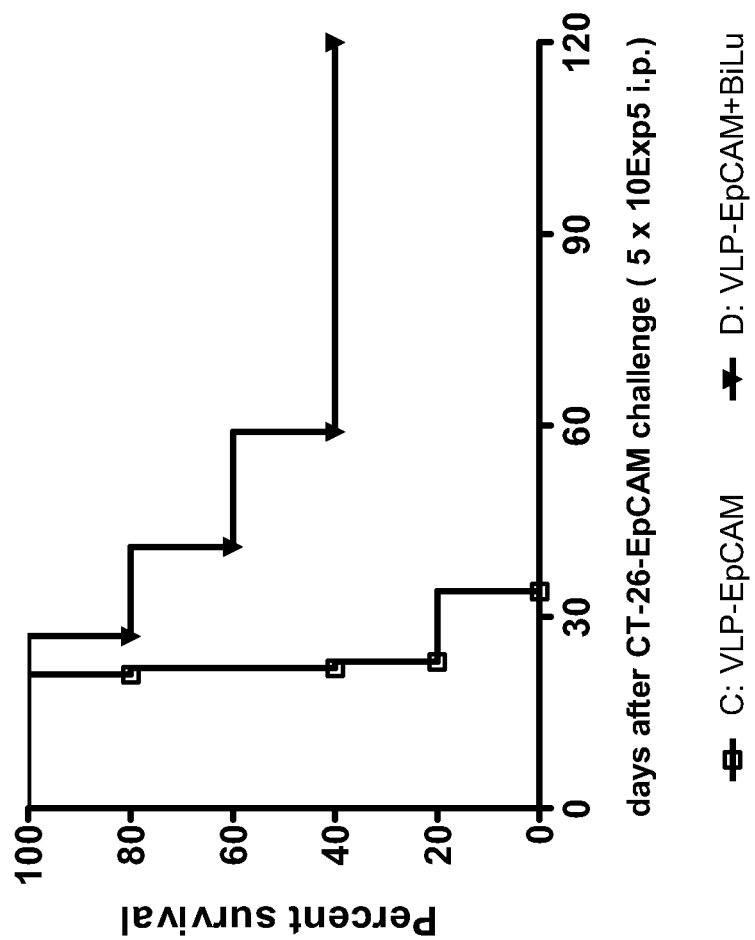

FIG. 7B: Survival of mice—immunization groups VLP-EpCAM vs. VLP-EpCAM+BiLu

Immunization group VLP-EpCAM+BiLu (n=5) shows significant prolonged survival in comparison to mice immunized with VLP-EpCAM only (n=5) after a lethal tumor challenge with CT26-EpCAM tumor cells (log-rank test, p=0.0066)

Figure 7C:
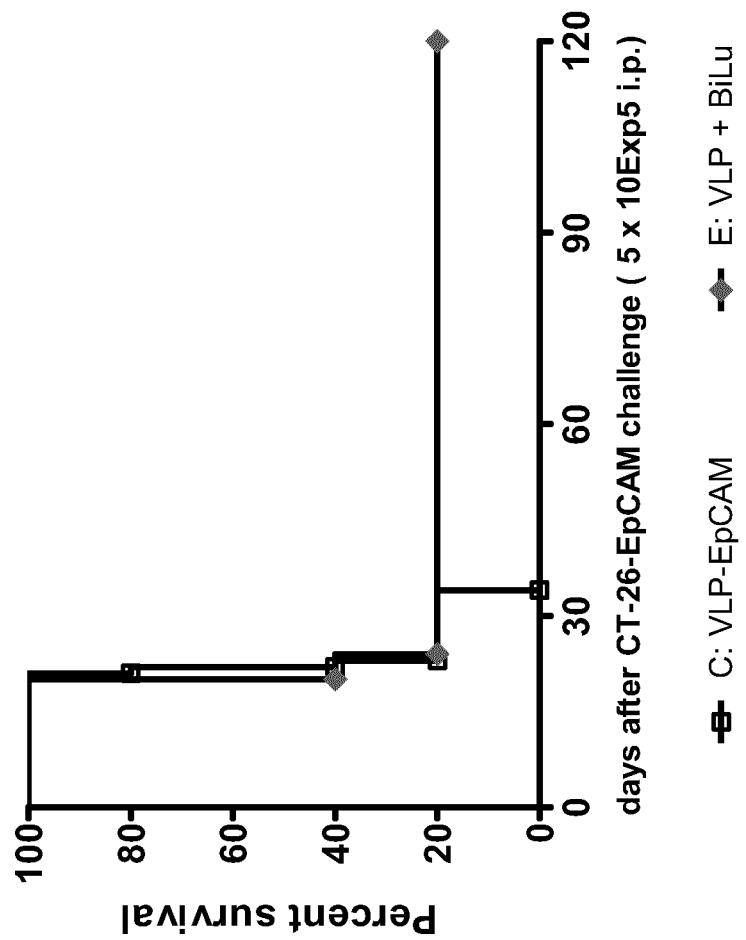

FIG. 7C: Survival of mice—immunization groups VLP-EpCAM vs. VLP+BiLu

Immunization group VLP-EpCAM (n=5) and the control group VLP+BiLu (n=5) that received no EpCAM protein showed no significant difference in survival curves (log-rank test, p=0.8237). All mice succumbed to the tumor except for one mouse in control group E indicating that there was no or only a minor unspecific immunization effect induced by the VLP and/or BiLu antibody.

SUMMARY OF THE INVENTION

The invention refers to a pharmaceutical composition comprising
a pharmaceutically effective amount of a trifunctional bispecific antibody having the following properties:
(a) binding to a T cell via CD3;
(b) binding to a target antigen which is present in solubilized form or in cryopreserved form or in particulate form;
(c) binding via its Fc-portion or by a third specificity (in the case of trispecific antibodies) to Fcγ-receptor type I, II and/or III positive cells and initiating the production of cytokines or upregulation of costimulatory signals or a combination thereof and thereby activating T cells;
(d) initiating interferon-gamma-accompanied TH1-biased T cell responses and humoral immune responses;
an immunologically effective amount of said target antigen and optionally further antigens which are present in solubilized or cryopreserved, e.g. lyophilized form or in particulate form, and
a pharmaceutically acceptable carrier
for use in a method of immunizing a mammal subject against diseases wherein said target antigen is involved, comprising administering to said subject a pharmaceutically effective amount of said pharmaceutical composition to evoke a cell-mediated or a humoral immune response or a combination thereof against said target antigen(s) to immunize said mammal subject against diseases wherein said target antigen(s) is (are) involved.

In a further embodiment of the invention, a pharmaceutical composition is described comprising a pharmaceutically effective amount of a trifunctional bispecific and/or trispecific antibody having the following properties:
(a) binding to a T cell via CD3;
(b) binding to a target antigen which is present in solubilized form or in cryopreserved form or in particulate form;
(c) binding via its Fc-portion or by a third specificity (in the case of trispecific antibodies) to Fcγ-receptor type I, II and/or III positive cells; and initiating the production of cytokines or upregulation of costimulatory signals or a combination thereof and thereby activating T cells;
(d) initiating interferon-gamma-accompanied TH1-biased T cell responses and humoral immune responses;
an immunologically effective amount of said target antigen which is present in solubilized or in cryopreserved, e.g. lyophilized form, or in particulate form, and a pharmaceutically acceptable carrier.

DETAILED DESCRIPTION OF PREFERRED EMBODIMENTS

Thus, the present invention describes an immunization method comprising adjuvant-like trifunctional bispecific or trispecific antibodies and vaccine formulations with the target antigen (i.e. heterologous fusion proteins, multi-antigen polypeptides, multi-epitope polypeptides, covalently or non-covalently linked protein antigens or virus-like-particles (VLPs) displaying conjugated or associated target antigens) wherein the target antigen or any additional further antigens are present in soluble or in cryopreserved form or in particulate form. All these embodiments cover only those antigens which are in isolated form, i.e. separated from their natural context, e.g. from a cell like a tumor cell, a bacterial cell, a fungal cell or a virus.

The target antigens and optionally further antigens are used in isolated form. The terms "isolated target antigen" and "isolated antigen" as used in the present invention have to be understood as comprising only those antigens which are not associated with and are not part of a cell. While they may have been present on a cell, e.g. on a tumor cell or a virus before their use in the present invention, they are not part of that cell or virus anymore when used in the present pharmaceutical composition. Typically, the antigens are used in soluble form; the term "solubilized" excludes those antigens which are associated with or bound to a cell, e.g. a tumor cell, or a natural occurring virus in the present pharmaceutical composition. If the antigens are not in soluble form, they are for example linked to, conjugated to or associated with a carrier, i.e. they are also in isolated but particulate form. A typical carrier is a virus-like particle (VLP) or a carrier antigen to which the target antigen is bound to or associated with. In a still further embodiment, the target antigen is present in isolated cryopreserved and preferably isolated soluble or isolated particulate form. The antibodies are also not present as heterocrosslinked antibodies.

In a preferred embodiment, the pharmaceutical preparation of the invention does not contain any immunologically active adjuvant, i.e. an immunologically active adjuvant is absent and is not administered to the patient during vaccination. It has been found that the trifunctional and trispecific antibodies as defined above and with the specific composition preferably used in the present invention trigger themselves an adjuvant-like effect making it superfluous to further add external adjuvants. Also the addition of external cytokines is not necessary and is excluded in the present invention as the presently used trifunctional and trispecific antibodies already trigger the production of cytokines per se.

Cryopreservation is a process by which the target antigens present in e.g. particulate or solubilised form are frozen under controlled conditions and stored at low temperatures. Cryopreservation is frequently used to store a sample which must be maintained over time in order to ensure a ready supply of the sample for use and experimentation. The target antigens for the purposes or the invention are routinely frozen in suspension in industrial cryo vials. Freezing methods have been developed to minimize the impact of osmotic shock and intracellular ice crystal formation, two factors that contribute to damage during the freezing process and frozen storage.

In general, a vaccine is a biological preparation that improves immunity to a particular infectious or malignant disease. A vaccine typically contains an agent that resembles a disease-causing microorganism or is derived from a cancer cell. The agent stimulates the body's immune system to recognize the agent as foreign, destroys it, and remembers it, so that the immune system can more rapidly recognize and destroy any of these microorganisms that it later encounters. In case of cancer diseases, it is absolutely required that relevant vaccines have to break already existing immune tolerance, especially T cell tolerance against self antigens for inducing anti-tumor efficacy. Such an approach would be an example for a therapeutic vaccination. Interestingly, trifunctional bispecific or trispecific antibodies with anti-CD3 binding arm have the capacity to break immune tolerance as secondary B and T cell responses are induced against self antigens (Ruf and Lindhofer et al., 2001; Ströhlein et al., J. Exp. Clin. Cancer Res. 28:18, 2009).

For purposes of the present invention, a "humoral immune response" refers to an immune response mediated by antibody molecules, while a "cellular immune response" or "cell-mediated immune response" is one mediated by T-lymphocytes and/or other white blood cells. A "protective immune response" is an immune response that inhibits a detrimental function or activity (such as a detrimental effect of a pathogenic organism such as a virus), reduces infection by a pathogenic organism (such as, a virus), or decreases symptoms that result from infection by the pathogenic organism. A protective immune response can be measured, for example, by the inhibition of viral replication or plaque formation in a plaque reduction assay or ELISA-neutralization assay (NELISA), or by measuring resistance to viral challenge in vivo.

Adjuvants

Vaccines can be prophylactic (e.g. to prevent or ameliorate the effects of a future infection by any natural pathogen), or therapeutic vaccines (e.g. for the treatment of chronic viral diseases like hepatitis B or hepatitis C or cancer). Mostly, vaccines are administered in combination with adjuvants augmenting the effects of a vaccine by stimulating the immune system to respond to the vaccine more vigorously, and thus providing increased immunity to a particular disease.

Thus, an adjuvant is an agent that may stimulate the immune system and increase the response to a vaccine. An immunologic adjuvant is defined as any substance that acts to accelerate, prolong, or enhance antigen-specific immune responses when used in combination with specific vaccine antigens.

Adjuvants accomplish immunostimulatory tasks by mimicking specific sets of evolutionarily conserved molecules, so called PAMPs (pathogen-associated molecular patterns), which include liposomes, lipopolysaccharides, molecular cages for antigens (i.e. nanoparticles, VLPs etc.), components of bacterial cell walls, and endocytosed nucleic acids such as double-stranded RNA, single-stranded DNA, and unmethylated CpG dinucleotide-containing DNA (Glenn and O'Hagan, 2007). Because immune systems have evolved to recognize these specific antigenic moieties, the presence of an adjuvant in conjunction with the vaccine can greatly increase the innate immune response to the antigen by augmenting the activities of dendritic cells, B and T lymphocytes, as well as macrophages by mimicking a natural infection. Furthermore, because adjuvants are attenuated beyond any function of virulence, they pose little or no independent threat to a host organism.

Aluminum salts (e.g. aluminum-hydroxyphosphatesulfate) were the first adjuvants approved by the U.S. Food and Drug Administration (FDA) for use in humans. Use of aluminum salts began in the 1930s, before regulatory guidelines became more stringent. More recently, approvals have been obtained in Europe for novel non-conventional adjuvant classes like MF59, an water-in-oil adjuvant component of influenza vaccine for elderly patients (Fluad®, Novartis Vaccines) or AS04 (combination of hydrated potassium aluminum sulfate and monophosphoryl lipid A (MPL), GlaxoSmithKline) as the adjuvant for a viral vaccine (hepatitis B, HBV).

For the improvement of immune responses induced by homologous or heterologous VLPs as well as protein antigens or any other vaccine encoding entity (i.e. DNA, RNA) novel more sophisticated adjuvant-like immunization strategies are required to address the following immunological and biotechnological issues:

The antigen-specificity of a novel adjuvant-like immunization strategy as conventional adjuvants is non-specific in stimulating immune responses.

Figure 1:
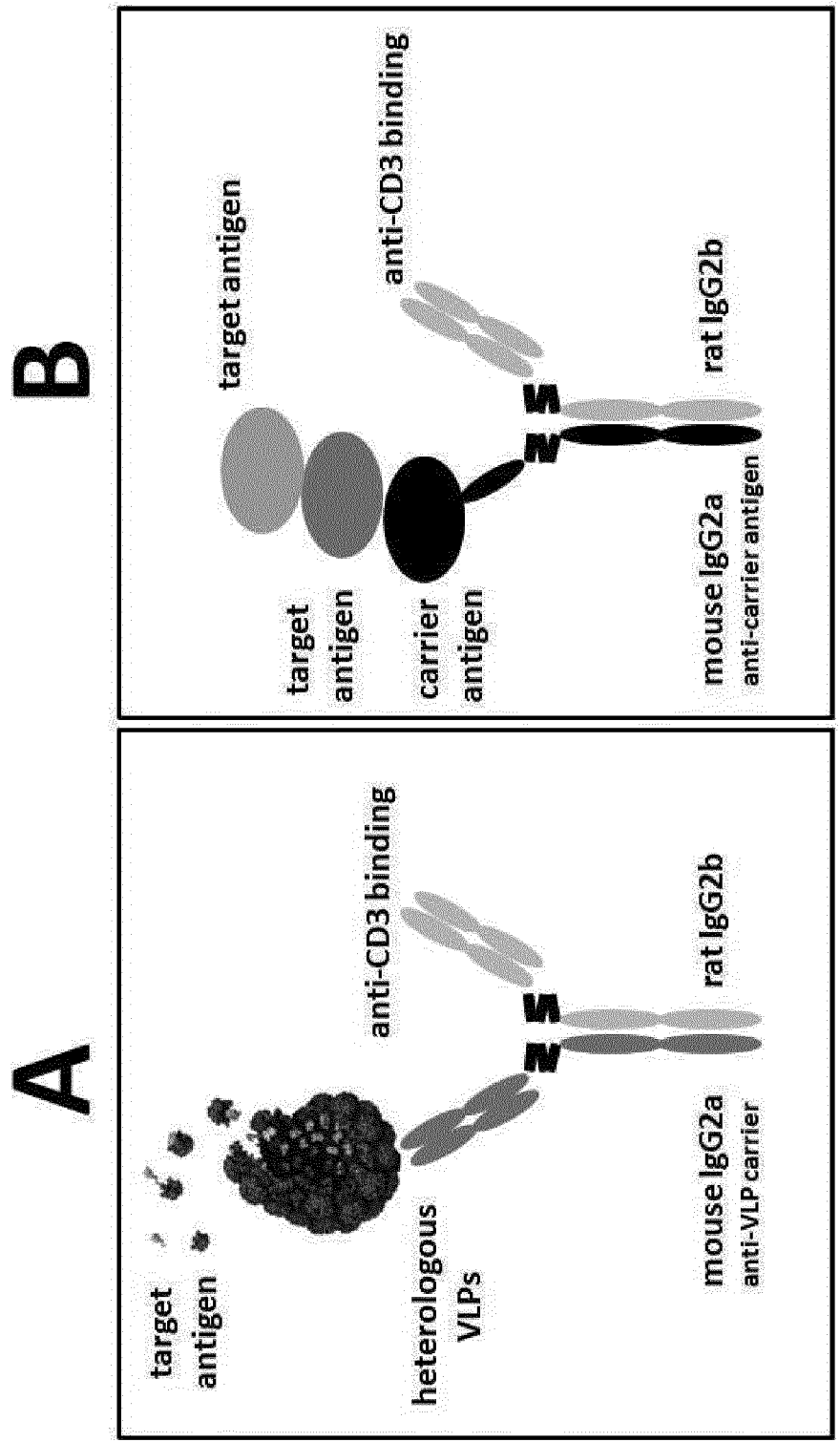
FIG. 1A: Heterologous virus-like-particles (VLPs) displaying target antigens for immunization
FIG. 1B: Heterologous fusion proteins, multi-antigen polypeptides or covalently linked protein antigens [i.e. fusion or conjugate format: single carrier antigen and single or multiple target antigen(s)]
Figure 2:
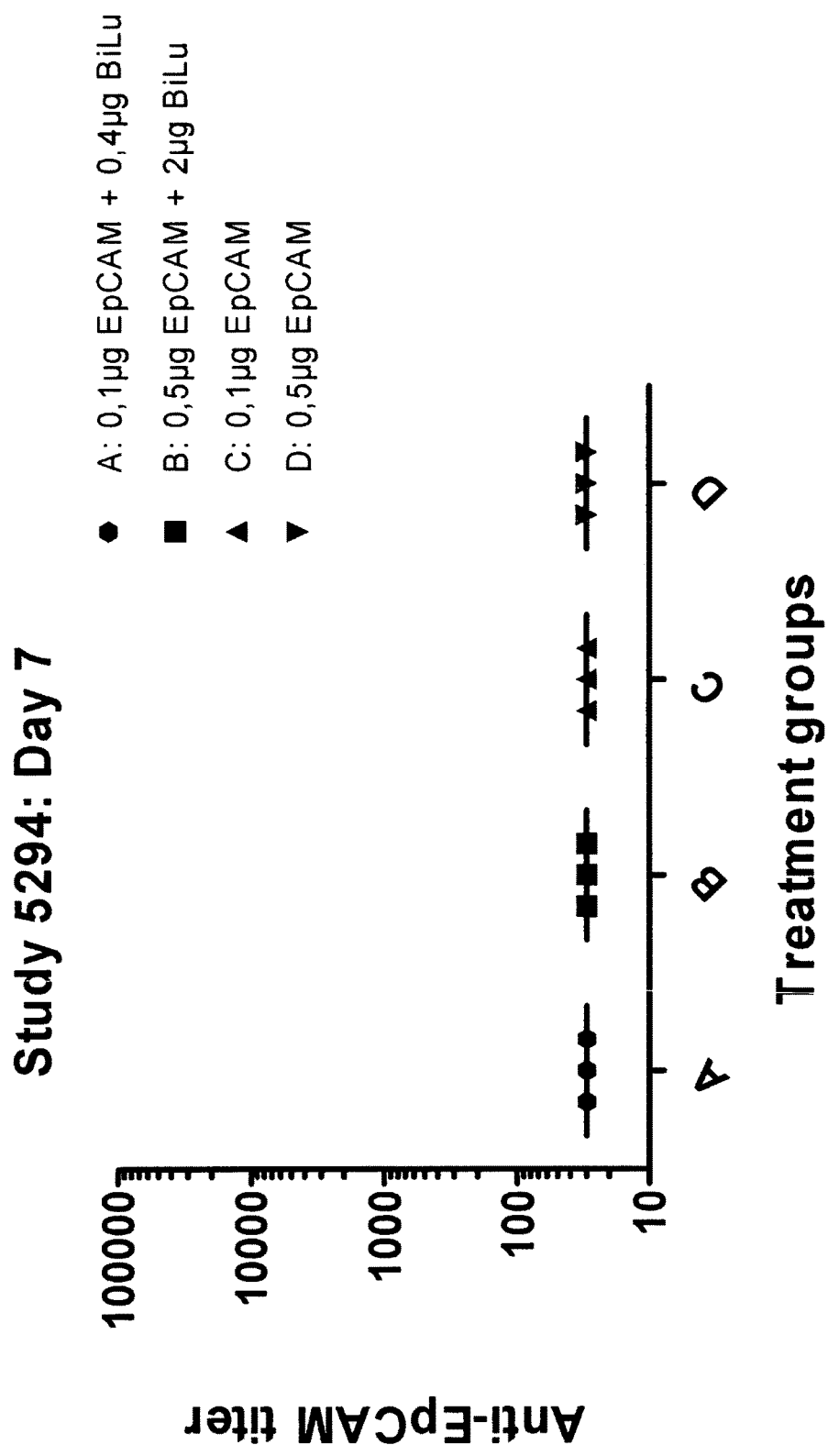
FIG. 2: Detection of mouse anti-EpCAM antibody titers in sera of differently immunized animals. Three BALB/c mice per group were s.c. immunized by using different amounts of recombinant human EpCAM protein antigens (0.1 μg or 0.5 μg) in absence or presence of 0.4 μg or 0.5 μg of anti-EpCAM×anti-CD3 antibody BiLu, respectively. Anti-EpCAM ELISA was performed as described in the method chapter.
Figure 2:
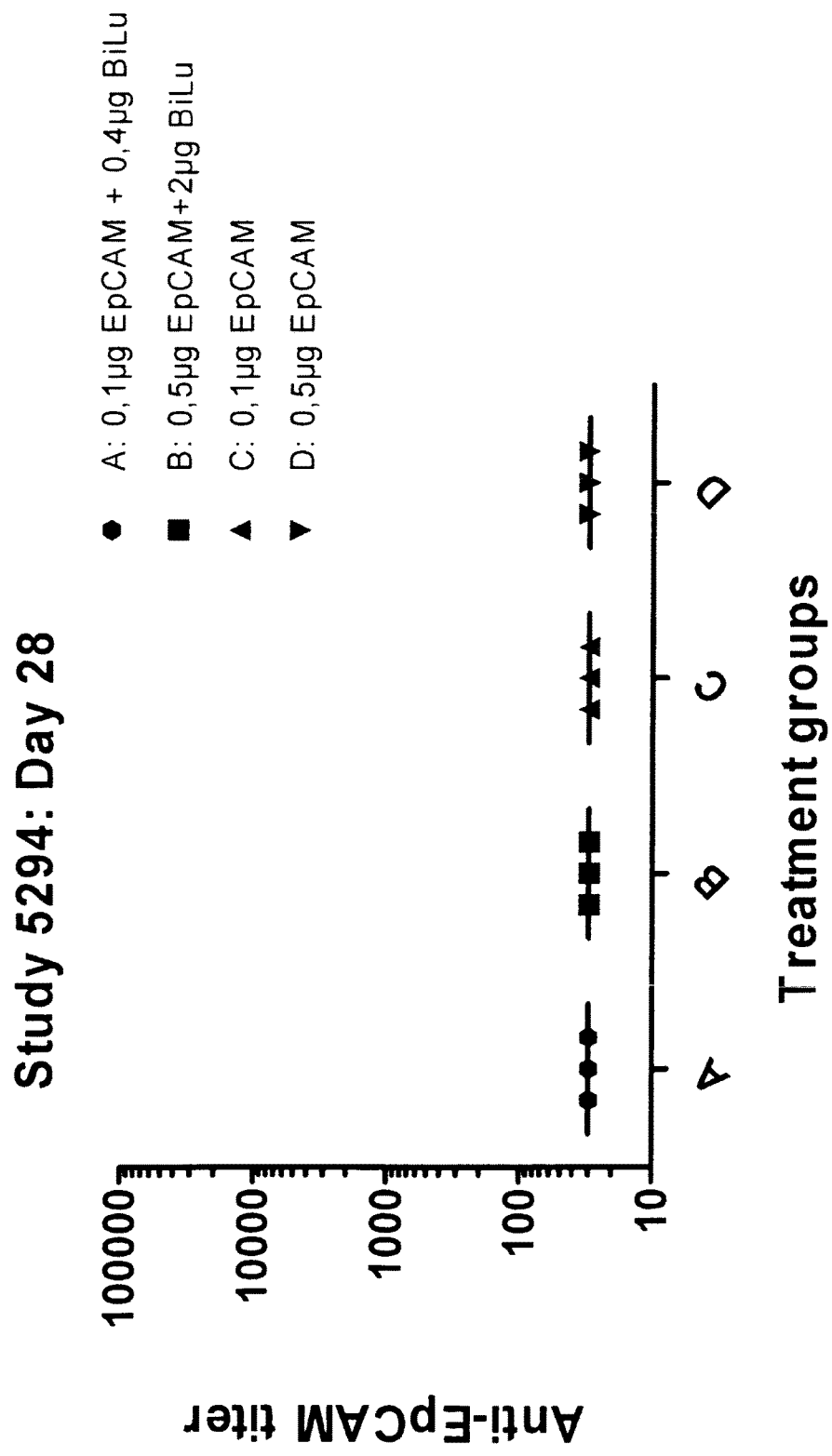
Figure 2:
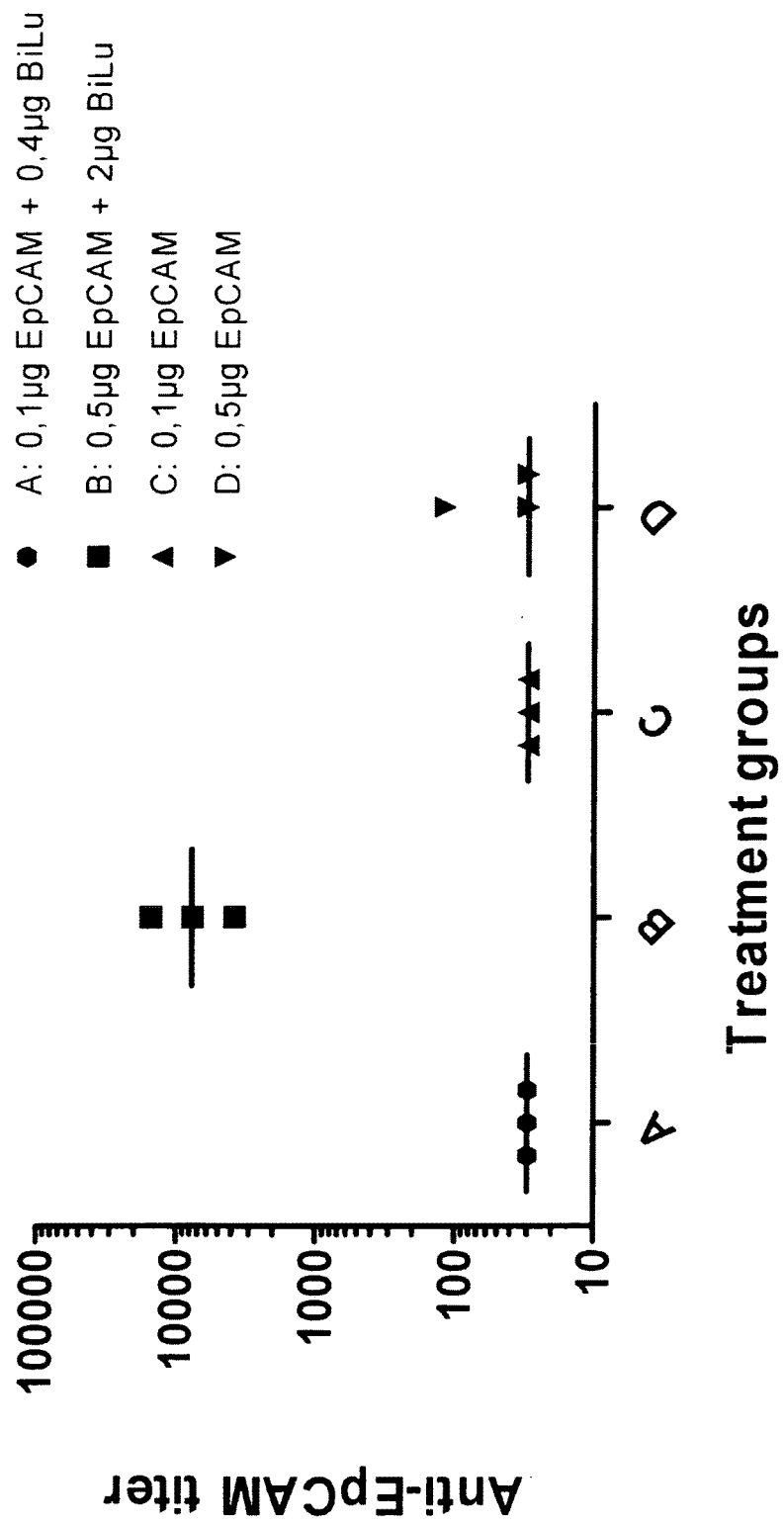
Figure 2:
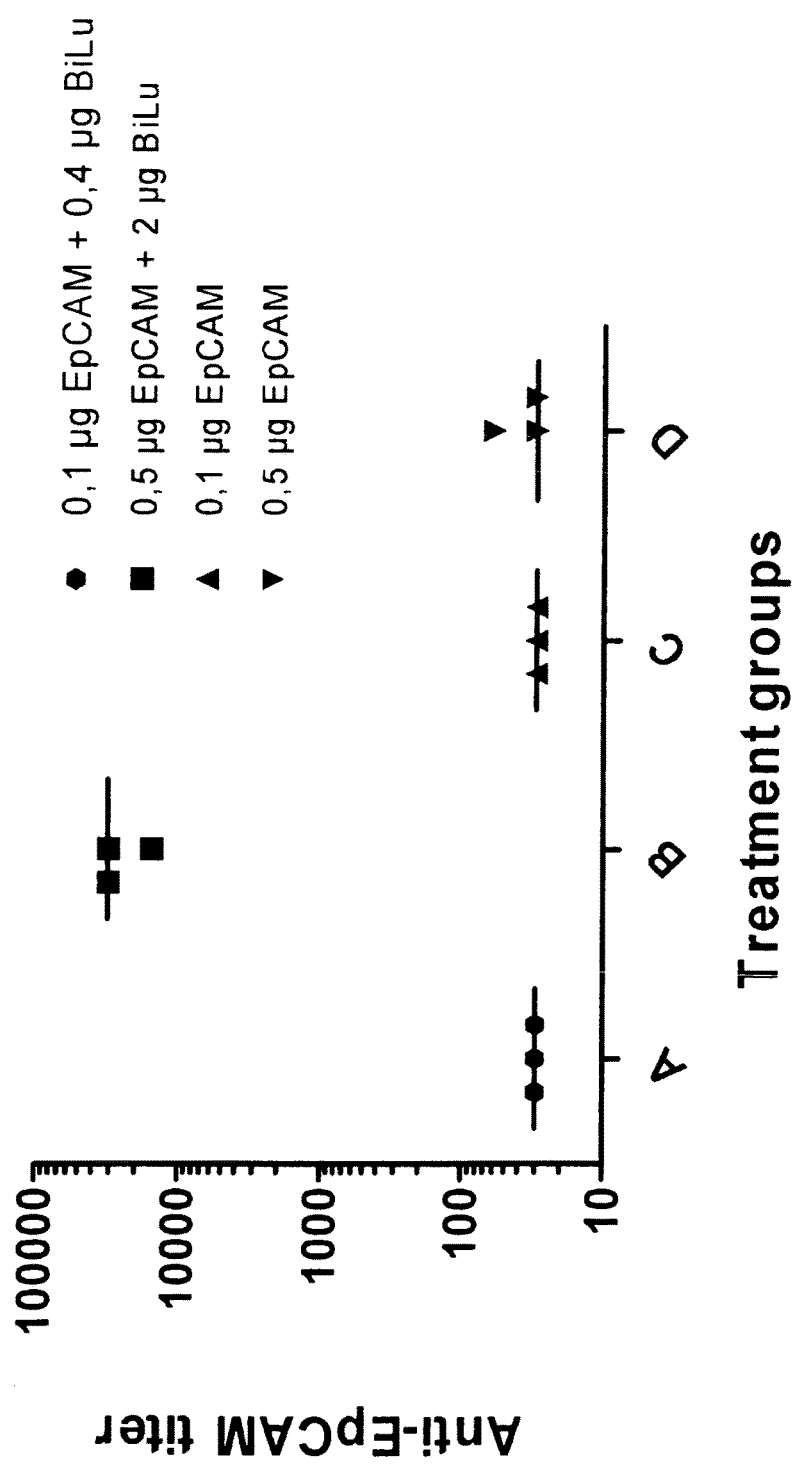

The feasibility of a platform technology concept with VLP carriers or carrier-proteins as universal targets to modulate antigen-specific immune responses (see also FIG. 1).

Predictability and straightforwardness of clinical development for appropriate vaccines in spite of trial and error combination approaches with non-antigen-specific adjuvant components.

Reduction of vaccine amounts used for immunization with comparable dose/response relationship as shown for conventional adjuvant settings.

Improvement of vaccine efficacy for non-responders (e.g. HBV vaccines) and opening up novel opportunities for therapeutic vaccination strategies.

According to a preferred embodiment of the invention no adjuvants have to be used, i.e. the pharmaceutical compositions and the therapeutic and prophylactic methods described herein are all preferably free of adjuvants, e.g. of the above and below referenced adjuvants. Examples of adjuvants which are generally used in the art and which are avoided in the present invention are inorganic adjuvants, e.g. aluminum salts like aluminum phosphate and aluminum hydroxide, organic adjuvants like squalene, and oil-based adjuvants.

The antibodies used in the present invention have been surprisingly found to make use of adjuvants superfluous as the second antigen binding arm of the trifunctional antibody used herein interacts with the target antigen which is present in solubilized or cryopreserved, e.g. lyophilized form, or which is present in particulate form, e.g. as surface-exposed VLP carrier epitope or an other appropriate carrier-protein epitope; all trifunctional bispecific and/or trispecific antibodies with activating Fc-gamma-receptor and mitogenic anti-CD3 recognition meet these important prerequisites for the presently described universal immunization strategy which can be used in the field of vaccine development (FIG. 1). In all cases, the antigens are free and not bound to or associated with e.g. a cell like a tumor cell.

Principle of the Invention

The present invention describes for the first time the capacity of said trifunctional and trispecific antibodies to induce antigen-specific humoral and/or cell-mediated immune responses (preferably both) against soluble or cryopreserved protein antigens or protein antigens present in particulate form instead of the conventional approach taken up to now in the prior art wherein the trifunctional antibody was always directed against an antigen associated with or bound to e.g. a tumor cell and not the isolated tumor antigen in cryopreserved form or in solubilized form or a target antigen which is present on a carrier in particulate form. The proinflammatory interferon-gamma driven TH1-biased cytokine milieu and the costimulatory signaling events required for the adjuvant-like immunization environment are induced in vivo via crosstalk of T cells and accessory cells activated by anti-CD3 and Fc-gamma-receptor engagement of said trifunctional bispecific and trispecific antibodies, respectively.

The inventor describes a new vaccination strategy and a pharmaceutical composition to be used for said vaccination utilizing the capacity of trifunctional bispecific and trispecific antibodies of (a) binding to a T cell and mediating a first activation signal thereto;
(b) binding to tumor-associated or specific antigens on a tumor cell or soluble proteins;
(c) binding, through its Fc portion (in the case of trifunctional bispecific antibodies) or a third specificity (in the case of trispecific antibodies) to Fc-gamma receptor I, II and/or III of Fc-gamma receptor-positive cells;
(d) activation of the Fc receptor-positive cell by binding to the Fc-gamma receptor-positive cell and, thereby initiating or increasing the expression of cytokines and/or up-regulating co-stimulatory antigens;
(e) transfer of at least one second activation signal required for physiological activation of the T cell to the T cell by the co-stimulatory antigens and/or cytokines, wherein said activation causes an up-regulation of activation markers, killing of the tumor cell, and/or T cell proliferation.

The pharmaceutical composition and the vaccination method of the invention are to be applied in the treatment of mammals, preferably of humans.

The inventors have found that a target antigen which is involved in a disease and which is administered in a pharmaceutical composition in solubilised form or in cryopreserved form or in particulate form specifically attached to a carrier like a VLP, can effectively trigger the immune system to induce a humoral and cell-mediated immune response directed against the target antigen and additionally to any other antigen which is administered in close proximity with the target antigen, preferably by being attached to the target antigen, e.g. in the form of a virus-like-particle. Therefore, it is not absolutely necessary that the antibody is directed against the antigen which is involved in or which is associated with a disease to be treated; it is also feasible that the antigen is directed against an epitope of a carrier protein which is not involved in a disease anyhow; as long as the disease involved antigen is applied in close relationship with the target antigen against which the antibody is directed, the immune system will be triggered by the antibodies of the present invention to induce a cell-mediated and humoral immune response which will also be directed against the disease involved antigen, e.g. a tumor-specific antigen. It is then supposed that the target antigen and the disease-associated (disease-involved) antigen are attached to each other directly or via a linker or via a carrier or via other proteins (cf. FIG. 1)

The target antigen does not necessarily need to be an antigen which is involved in the treatment of a disease like a tumor, a viral or bacterial or fungal infection etc. The target antigen may also be an antigen which is specific for the carrier or any other entity against which the antibody is directed. In said case the target antigen together with the trifunctional bispecific or trispecific antibody will act as a kind of adjuvant and initiate a humoral and cell-mediated immune response which will also assist to immunize the individual to be treated against the disease-specific antigen. On the molecular and cellular level this similar reactiveness towards different protein species is simply reflected by the aggregate structure originated from covalently linked or associated protein entities that is phagocytozed, processed and presented to T cells via a single APC in context of the immunostimulatory environment which is created by the presently used trifunctional bispecific and trispecific antibodies. Said immunostimulatory environment involves activation of the Fc-receptor-positive cell by binding to the Fcgamma-receptor-positive cell and initiating or increasing the expression of cytokines and/or co-stimulatory antigens; secondly, at least a second activation signal required for physiological activation of the T cell will be transferred to the T cell by the co-stimulatory antigens and/or cytokines or vice versa from the T cell to the accessory cell, wherein said activation causes an up-regulation of activation markers, killing of the tumor cell, and/or T cell proliferation. It is to be emphasized that the present use of the antibodies covered by the invention avoids the external addition of cytokines like interleukins as these antibodies themselves initiate production of cytokines by activating Fcgamma-receptor-positive cells.

Target Antigens

A "target antigen" or briefly and interchangeably described as "antigen" is a compound, composition, or substance that can stimulate the production of antibodies or a T cell response in an animal or human being, including compositions that are injected or absorbed into an animal or human being. An antigen reacts with the products of specific humoral or cellular immunity.

An "antigenic polypeptide" (interchangeably used with "target antigen") is a polypeptide to which an immune response, such as a T cell response or an antibody response, can be stimulated. The term "target antigen" includes also related antigenic epitopes. "Epitope" or "antigenic determinant" refers to a site on an antigen to which B and/or T cells respond. Epitopes can be formed both from contiguous amino acids (linear) or non-contiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, an epitope will include between about 5 and 15 amino acids, such as, 7, 9, 10, 12 or 15 amino acids. The amino acids are in a unique spatial conformation. Methods of determining spatial conformation of epitopes include, for example, x-ray crystallography and multi-dimensional nuclear magnetic resonance spectroscopy. Methods of determining spatial conformation of epitopes include, for example, x-ray crystallography and multi-dimensional nuclear magnetic resonance spectroscopy. See, e.g., "Epitope Mapping Protocols" in Methods in Molecular Biology, Vol. 66, Glenn E. Morris, Ed (1996).

The term "target antigen" denotes both subunit antigens, (for example, antigens which are separate and discrete from a whole organism with which the antigen is associated in nature), as well as killed, attenuated or inactivated bacteria, viruses, fungi, protozoa, parasites or other microbes and also immunologically active epitopes of anyone of these antigens.

An "antigen" includes a protein with modifications, such as deletions, additions and substitutions (generally conservative in nature) to the native sequence, so long as the protein maintains the ability to elicit an immunological response, as defined herein. These modifications may be deliberate, as through site-directed mutagenesis, or may be accidental, such as through mutations of hosts which produce the antigens.

Said target antigen may be a disease-associated antigen selected from one or more members of the group consisting of tumor-associated antigens, fungal antigens, viral antigens, protozoan and bacterial antigens, and/or said target antigen is a carrier-specific but non-disease associated antigen wherein the disease-associated antigen is conjugated to or associated with said carrier, and/or said target antigen is a non-disease associated antigen conjugated to or associated with one or more disease associated antigens, and/or an immunologically active epitope of anyone of said target antigens.

In one embodiment of the invention, the target antigen is a tumor-associated antigen. Generally all kinds of tumors can be treated by the present method. Particularly epithelial tumors, adenocarcinomas, colon carcinomas, mamma carcinomas, ovarial carcinomas, carcinomas of the lungs, throat, nose and ear can be treated. Furthermore, preferably non-epithelial tumors like leukemias and lymphomas and virus inducted tumors like liver tumors or cervix carcinomas can be treated. Examples for tumor-associated antigens to be used are EpCAM, Her2/neu, MAGE-A2, MAGE-A3, MAGE-A5, MAGE-AX, NY-ESO-1, NFX2, SSX2, SSX4, Trp2, gp100, tyrosinase, Muc-1*, CEA, telomerase, survivin, CD20, G250, proteoglycans, p53, EGF-R, CA125, MUC, Wue antigen, Lewis Y antigen, HSP-27, HSP-70, HSP-90, PSA, PMSA, GD2, GD3, FAP, Pgp, MCSP, EpHA2, CD33 and cell surface targets GC182, GT468 or GT512.

The tumor-associated antigens described above are associated with or specific for particular tumors. E.g. EpCAM is typically associated with adenocarcinomas, Her2/neu with mamma carcinomas but also with colon, lung, gastric, pancreas and ovarian cancer, CD20 with B cell lymphomas like non-Hodgkin's lymphoma or chronic lymphotic leukemia, G250 with renal carcinomas, proteoglycans, GD3 and GD2, gp100, tyrosinase with melanomas, EGF-R and CEA with epithelial tumors.

Further antigens to be used are antigens of human viruses, e.g. HBsAg or HBcAg of hepatitis B or hepatitis C virus, gp41, gp120 or nef of HIV-1, L1 of papillomavirus, HA and NA of influenza virus; bacterial antigens, e.g. Ag85B or ESAT-6 of *Mycobacterium tuberculosis*; fungal antigens, e.g. mannoprotein 65 or Hsp90 of *Candida albicans*, Hsp60 or histon-$H_2$B-like surface protein of *Histoplasma capsulatum*, capsular polysaccharide GXM of *Cryptococcus neoformans*; protozoal antigens, e.g. circumsporozoite protein, MCSP-1, var, PfEMB1 or AMA1/MSP-1 of *Plasmodium* spp., GST or tetraspanin or paramyosin of *Schistosoma* spp., gp63 or PSA-2.

Summarily, said disease-associated target antigen are e.g. selected from one or more members of the group consisting of EpCAM, Her2/neu, PMAGE-A3, NY-ESO-1, TRP2, gp100, Muc-1*, CEA, MUC, MAGE-A2, MAGE-A3, MAGE-A5, MAGE-AX, NFX2, SSX2, SSX4, tyrosinase, telomerase, survivin, CD20, G250, proteoglycans, p53, EGF-R, CA125, Hsp 27, Hsp70, Hsp90, PSA, PMSA, Wue antigen, Lewis Y antigen, FAP, Pgp, MCSP, EpHA2, CD33, cell surface targets GC182, GT468, GT512, viral antigens: HA and NA of influenza virus; HBsAg and HBcAg of HBV or HCV, L1 of papillomavirus, HIV1-specific gp 41, gp120 or nef, bacterial antigens: Ag85B or ESAT-6 of *Mycobacterium tuberculosis*; fungal antigens: e.g. mannoprotein 65 or Hsp90 of *Candida albicans, Hsp*60 or histon-$H_2$B-like surface protein of *Histoplasma capsulatum*, capsular polysaccharide GXM of *Cryptococcus neoformans*; protozoal antigens, e.g. circumsporozoite protein or AMA1/MSP-1 or PfEMP1 or var of *Plasmodium* spp., GST or tetraspanin or paramyosin of *Schistosoma* spp., gp63 or PSA-2.

Said target antigen and/or one or more of said additional further antigens are present in isolated, non-conjugated form, or said target antigen is conjugated to or associated with a carrier or wherein said target antigen and said one or more further antigens are associated or conjugated with each other directly or via a carrier, optionally wherein said target antigen is displayed by a virus-like-particle.

Said target antigen may also be a carrier-specific but non-disease associated antigen wherein the disease-associated antigen is conjugated to or associated with said carrier.

Said target antigen may also be a non-disease associated antigen conjugated to or associated with one or more disease associated antigens.

Said carrier for association or conjugation with said target antigen and/of further antigens may be selected from the group consisting of homologous VLPs, heterologous/chimeric VLPs with covalently linked or associated protein antigens, single protein antigens, multi-antigen polypeptides, heterologous fusion proteins.

Form of Administration of the Target Antigens in Combination with the Trifunctional Bispecific or Trispecific Antibodies The target antigens are administered in one embodiment of the invention in the form of a solubilized protein and in the absence of an adjuvant in a pharmaceutical preparation in combination with a trifunctional bispecific or trispecific antibody and pharmaceutically compatible carriers. "Solubilized protein" means that the target antigen is for instance not present on a cell, e.g. a tumor cell, but either in an in water or physiological saline soluble form. The solubility of a target antigen protein is dependent inter alia from the isoelectric point and the ion strength. Globular proteins are quite easily soluble in water or physiological saline. The higher the number of hydrophilic groups at the target antigen protein surface the bigger is the solvation shell formed and the better is its solubility.

Virus-Like Particles

In a further embodiment of the invention the target antigens are presented on the surface of virus-like particles (VLPs). Virus-like particle (VLP), as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell.

A virus-like particle in accordance with the invention is non-replicative and/or non-infectious since it lacks preferably all or part of the viral genome or genome function. In one embodiment, a virus-like-particle is a virus particle, in which the viral genome has been physically or chemically inactivated. Typically and more preferably a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA bacteriophage. The terms "viral capsid" or "capsid", refer to a macromolecular assembly composed of viral protein subunits. Typically, there are 60, 120, 180, 240, 300, 360 and more than 360 viral protein subunits. Typically and preferably, the interactions of these subunits lead to the formation of viral capsid or viral-capsid like structure with an inherent repetitive organization, wherein said structure is, typically, spherical or tubular. For example, the capsids of RNA bacteriophages or HBcAgs have a spherical form of icosahedral symmetry. The term "capsid-like structure" as used herein, refers to a macromolecular assembly composed of viral protein subunits resembling the capsid morphology in the above defined sense but deviating from the typical symmetrical assembly while maintaining a sufficient degree of order and repetitiveness.

One common feature of virus particle and virus-like particle is its highly ordered and repetitive arrangement of its subunits. Virus-like particle of an RNA bacteriophage: As used herein, the term "virus-like-particle of an RNA bacteriophage" refers to a virus-like particle comprising, or preferably consisting essentially of or consisting of coat proteins, mutants or fragments thereof, of an RNA bacteriophage. In addition, virus-like particle of an RNA bacteriophage resembling the structure of an RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. This definition should, however, also encompass virus-like particles of RNA bacteriophages, in which the aforementioned gene or genes are still present but inactive, and, therefore, also leading to non-replicative and/or non-infectious virus-like particles of an RNA bacteriophage.

Preferred VLPs derived from RNA bacteriophages exhibit icosahedral symmetry and consist of 180 subunits (monomers). Preferred methods to render a virus-like particle of an RNA bacteriophage non replicative and/or non-infectious is by physical, chemical inactivation, such as UV irradiation, formaldehyde treatment, typically and preferably by genetic manipulation.

Typically, the virus-like-particles are heterologous as they contain as foreign heterologous protein at least one target antigen which is presented (displayed) by the VLP on its surface to the antibody which is capable of binding to said target antigen. The VLP acts like a carrier displaying the target antigen entity.

Target antigens in particulate form according to the invention which are in the form of VLPs generally comprise different essential proteins and one or more further optional proteins. In one embodiment at least the essential proteins are virus major inner capsid proteins, one of said essential proteins is a virus major outer capsid protein, and the optional proteins are selected from minor inner capsid proteins and major outer capsid proteins. Preferably the VLPs comprise zero, or one further optional virus major outer capsid proteins and/or zero, one, two or three further optional virus minor inner capsid proteins.

The aforementioned proteins are chimeric and comprise an amino acid sequence derived from a foreign protein other than or identical with said native proteins wherein said chimeric or native amino acid sequence forms the target amino acid sequence for the binding of the trifunctional bispecific antibodies of the invention.

Hence at least one of any of the aforementioned proteins is chimeric and comprises an amino acid sequence derived from a foreign protein other than the native proteins.

The antigens of the invention may be produced with at least one of the proteins in native form and the same protein or proteins additionally being in chimeric form, i.e. incorporating amino acid sequences of a foreign protein. Chimeric antigens in particulate form may be produced according to the invention wherein the amino acid sequence derived from the foreign protein includes an epitope which is recognized by a trifunctional bispecific antibody to the foreign protein. For example, the foreign protein is a protein of a disease-producing organism and the antigen in particulate form is capable of raising protective (e.g. neutralizing) antibodies and/or cellular immune response in an organism susceptible to the disease. The antigens used in the invention find special utility in the formulation of vaccines.

Chimeric VLPs may include one or more of the incorporated major structural proteins in chimeric form. The VLPs may include at least one or two or more different virus proteins in native form, and at least one protein in chimeric form comprising an amino acid sequences from an amino acid sequence derived from a foreign protein.

Chimeric VLPs comprising at least one non-native protein are produced according to the invention by assembling the VLPs from a plurality of different proteins including native virus proteins and the non-native protein. The non-native protein comprises an amino acid sequence derived from a foreign protein and an amino acid sequence derived from a native virus protein. The amino acid sequence derived from a foreign protein may be located at the N-terminal end of the chimeric protein, although other arrangements are also envisaged according to the invention, for example wherein the amino acid sequence derived from a foreign protein is inserted within the sequence of the native protein, or is located at the C-terminal end. It has been found that locating the amino acid sequence derived from a foreign protein at the N-terminal end of the chimeric protein enables the foreign epitope to be immunogenic in the VLP.

Conventional techniques of site-directed mutagenesis and gene splicing may be employed in order to construct DNA sequences capable of being expressed as the chimeric protein included as a component of the antigen particles of the invention. Similarly the antigen particles may be assembled from their constituent components in a variety of ways. Thus, for example, the components may be produced separately and then simply combined by mixing solutions of the constituent proteins in a suitable medium. However, it is preferred that the native and chimeric proteins are expressed together so that assembly of the antigen particles can take place without the expressed polypeptide being degraded, modified or otherwise altered.

In one embodiment of the invention, the tumor specific anitgen EpCAM is crosslinked with a VLP and administered to an individual in order to induce an IFNgamma-CD8 T cell response and protection against EpCAM-specific tumors.

In further alternative embodiments of the invention, the target antigen is displayed in the form of a heterologous fusion protein, multi-antigen polypeptide, multi-epitope polypeptide, or a covalently linked protein antigen.

The term "heterologous fusion protein," is to be understood as a protein which is composed of at least two proteins which are different from each other and which are covalently linked (i.e. fused) together. At least one component of said fusion protein acts as the target antigen while the other one is a further antigen against which the individual is to be immunized. It is to be noted that the target antigen is generally said antigen against which the individual is to be immunized.

The term "multi-antigen polypeptide" is to be understood as a polypeptide which is composed of at least two polypeptides which are different from each other and which are preferably covalently linked (i.e. fused) together. At least one component of said polypeptide acts as the target antigen while the other one is defined as "one or more further antigen" against which the individual is to be immunized. It is to be noted that the target antigen is generally said antigen against which the individual is to be immunized.

The term "multi-epitope polypeptide" is to be understood as a polypeptide which is composed of at least two peptides defining epitopes which are different from each other and which are preferably covalently linked together. At least one epitope of said polypeptide acts as the target antigen while the other one is defined as "one or more further antigen" against which the individual is to be immunized. It is to be noted that the target antigen is generally said antigen against which the individual is to be immunized.

The term "covalently linked protein antigen" is to be understood as a protein antigen which is covalently linked to any entity, e.g. a virus-like particle, a bacteriophage, a carrier etc.

It is emphasized that the target antigen and the one or more further antigens against which the mammal subject is to be immunized are not present in the form of cells, specifically not in the form of complete cells. Any carrier to which the target antigen is bound is present in a size which is within a medium diameter of about 10 nm to 1 μm. Contrary thereto, the antibody-mediated therapies of the prior art made use of complete cells which seize is in the range of about 10-30 μm, i.e. much bigger than the seize of the target antigen used in the invention.

"Particulate form" is to be understood as any particle of any shape with a medium diameter of about 10 to 1000 nm. Specific examples are virus-like-particles, bacteriophages, artificial, e.g. polymeric particles, etc.

Antibodies

According to the invention, heterologous intact trifunctional bispecific and/or trispecific antibodies (trAbs) are used in one specific and preferred embodiment of the invention. These antibodies are intact, i.e. have a functional Fc portion, and they must be heterologous in nature, i.e. they must consist of heavy immunoglobulin chains of different subclasses (subclass combinations, also fragments) and/or origin (species).

These intact heterologous trifunctional bispecific and/or trispecific antibodies will be selected to further have the following properties: a) binding to a T cell; b) binding to at least one antigen on a tumor cell; c) binding, by their Fc portion (in the case of bispecific antibodies), or by a third specificity (in the case of trispecific antibodies) to Fc receptor-positive cells. Preferably, they also initiate interferon-gamma-accompanied TH1-biased T cell responses and humoral immune responses.

Activation of the Fc receptor-positive cells by the trAb depends on the subclass or subclass combination, respectively, of the trAb. As demonstrated in in vitro experiments, for example trAbs of the subclass combination mouse IgG2a/rat IgG2b are able to bind simultaneously to and activate Fc receptor-positive cells leading to up-regulation and formation (expression), respectively, of co-stimulatory antigens, such as CD40, CD80, or CD86, on the cell surface of such cells. In contrast, bsabs of the subclass combination mouse IgG1/IgG2b are able to bind to Fc receptor-positive cells (1) but clearly are unable to activate these cells to a comparable extent (2).

While the trAbs at the same time bind to and activate the T cell via one of binding arms (e.g. to CD3 or CD2), co-stimulatory signals derived from the Fc receptor-positive cell bound to the Fc portion of the trAb may be transferred to the T cell. I.e. only the combination of T cell activation via one binding arm of the trAb and the concomitant transfer of co-stimulatory signals from the Fc receptor-positive cell to the T cell results in an effective T cell activation.

A further important aspect in the induction of anti-tumor immunity is the possibility of phagocytosis, processing and presentation of tumor components by accessory cells (monocytes/macrophages, dendritic cells, and NK-"natural killer"-cells) which have been directed and activated by the bsAb. By this classical mechanism of antigen presentation tumor-specific CD4 cells as well as CD8 positive cells can be generated. Moreover, tumor-specific CD4 cells play an important role in the induction of a humoral immune reaction in the context of the T-B cell cooperation.

Trifunctional bispecific and trispecific antibodies are able to bind to the T cell receptor complex of the T cell by one binding arm and to tumor-associated antigens by the second binding arm. Thereby, they activate T cells which destroy the tumor cells by releasing cytokines or apoptosis-mediating mechanisms. Furthermore, in the context of their activation by bispecific antibodies it is clearly possible for T cells to recognize tumor-specific antigens via their receptor whereby a long-lasting immunization is initiated. In this respect, the intact Fc portion of the bispecific or trispecific antibodiy is of particular importance mediating the binding to accessory cells such as monocytes/macrophages and dendritic cells and inducing these cells to become themselves cytotoxic and/or simultaneously transfer important co-stimulatory signals to the T cell. In this manner, it seems to be possible that a T cell reaction may be induced also against so far unknown tumor-specific peptides.

Redirection of possibly anergized tumor-specific T cells to tumor cells by means of bispecific and/or trispecific antibodies and concomitant co-stimulation of such T cells by accessory cells bound to the Fc portion of the bispecific or trispecific antibody might act to reverse the anergy of cytotoxic T cells (CTLs); i.e. using intact heterologous bispecific and/or trispecific antibodies a T cell tolerance existing in the patient against the tumor may be neutralized and, thereby, a long-lasting anti-tumor immunity may be induced.

The antibodies used according to the invention are preferably able to reactivate tumor-specific T cells being in an anergic state. Further, they are able to induce e.g. tumor-reactive complement-binding antibodies and thereby a humoral immune reaction.

Binding of the trAbs preferably takes place via CD3, CD2, CD4, CD5, CD6, CD8, CD28, and/or CD44 to the T cell, most preferred via CD3. Fc receptor-positive cells at least bear an Fcgamma receptor I, IIa, IIb or III.

The antibodies employed according to the invention are able to bind to monocytes, macrophages, dendritic cells, "natural killer" cells (NK cells) and/or activated neutrophils all being Fcgamma receptor I-positive cells.

The antibodies used according to the invention lead to an induction or increase in the expression of CD40, CD80, CD86, ICAM-1, and/or LFA-3 as co-stimulatory antigens and/or cytokine secretion by the Fc receptor-positive cell. The cytokines preferably are IL-1, IL-2, IL-4, IL-6, IL-8, IL-12, and/or TNF-[alpha].

Binding to the T cell takes place via the T cell receptor complex of the T cell.

The trifunctional bispecific antibodies used according to the invention preferably are an anti-CD3×anti-tumor-associated antigen antibody and/or anti-CD4×anti-tumor-associated antigen antibody and/or anti-CD5×anti-tumor-associated antigen antibody and/or anti-CD6×anti-tumor-associated antigen antibody and/or anti-CD8×anti-tumor-associated antigen antibody and/or anti-CD2×anti-tumor-associated antigen antibody and/or anti-CD28×anti-tumor-associated antigen antibody and/or anti-CD44×anti-tumor-associated antigen antibody. Particularly preferred is an anti-CD3×anti-tumor-associated antigen antibody Preferred are trifunctional antibodies with the following group of isotype combinations in its Fc-region:
rat-IgG2b/mouse-IgG2a,
rat-IgG2b/mouse-IgG2b,
rat-IgG2b/human-IgG1,
mouse-[VH-CH1,VL-CL]-human-IgG1/rat-[VH-CH1,VL-CL]-human-IgG1-[hinge]-human-IgG3*-[CH2-CH3]
wherein *=caucasian allotypes G3m(b+g)=no binding to protein A.

Particularly preferred is rat-IgG2b/mouse-IgG2a, further preferred in combination with anti-CD3.

Preferably said trifunctional bispecific antibody is an anti-target-antigen×anti-CD3 antibody binding to Fcγ-type I/II/III-receptors with the isotype combination rat-IgG2b/mouse-IgG2a.

The antibodies are monoclonal, chimeric, recombinant, synthetic, semi-synthetic or chemically modified intact antibodies having for example Fv, Fab, scFv or F(ab)2 fragments.

The preparation of monoclonal antibodies preferably originating from mammals, e.g. methods, as for example described in Köhler and Milstein (Nature 256 (1975), 495), in Harlow and Lane (Antibodies, A Laboratory Manual (1988), Cold Spring Harbour) or in Galfré (Meth. Enzymol. 73 (1981), 3). Furthermore, it is possible to prepare the antibodies described by means of recombinant DNA technology according to techniques obvious to the skilled artisan (see Kurucz et al., J. Immunol. 154 (1995), 4576; Hollinger et al., Proc. Natl. Acad. Sc. USA 90 (1993), 6444). The antibodies used in the present method can be designed and manufactured by a person skilled in the art without undue burden; e.g. Greenwood et al. disclose the exchange of single immunoglobulin domains (for instance $CH_2$) by suitable cloning technique. By using these cloning technique antibody combinations like mouse-[VH-CH1,VL-CL]-human-IgG1/rat-[VH-CH1,VL-CL]-human-IgG1-[hinge]-human-IgG3*-[CH2-CH3]
wherein *=caucasian allotypes G3m(b+g)=no binding to protein A.

On the one hand, the preparation of trifunctional bispecific antibodies may be performed using recombinant DNA technology or by hybrid-hydridoma fusion technique (see for example Milstein et al., Nature 305 (1983), 537). By this technique, hybridoma cell lines producing antibodies each having one of the desired specificities are fused, and recombinant cell lines producing antibodies with both specificities are identified and isolated.

The preparation of antibodies having three specificities, so-called trispecific antibodies, may be carried out by coupling to one of the heavy IgG chains of a bispecific antibody a third antigen-binding site having another specificity, e.g. in the form of "single chain variable fragments" (scFv). The scFv may be for example bound to one of the heavy chains via a -S-S(G4S)nD-I linker [0105] (S=serine, G=glycine, D=aspartate, I=isoleucine).

Analogously, trispecific F(ab)2 constructs may be prepared substituting the CH2-CH3 regions of the heavy chain of one specificity of a bispecific antibody by a scFv of a third specificity while the CH2-CH3 regions of the heavy chain of the other specificity are removed, e.g. by introduction of a stop codon (at the end of the "hinge" region) into the coding gene for example by homologous recombination. For the preparation of trispecific scFv constructs, three VH-VL regions representing three different specificities are arranged in series.

For the sake of complete disclosure, reference is made for instance to U.S. Pat. No. 6,994,853 which is incorporated herein by reference completely.

The problem underlying the invention may be solved both by preferably trifunctional bispecific and by trispecific antibodies insofar as they show the features and activities characterized in claim 1. In the following, the preparation of antibodies having two and three specificities is described in more detail. To provide said trifunctional bispecific and trispecific antibodies belongs to the state of the art, and the literature describing such methods of preparation is hereby incorporated by reference in its entirety. The preparation of antibodies having three specificities, so-called trispecific antibodies, which are also suitable to solve the fundamental problem of the invention may be for example carried out by coupling to one of the heavy IgG chains of a bispecific antibody a third antigen-binding site having another specificity, e.g. in the form of "single chain variable fragments" (scFv). The scFv may be for example bound to one of the heavy chains via a-S-S(G4S)nD-I linker (S=serine, G=glycine, D=aspartate, I=isoleucine).

Analogously, trispecific F(ab)2 constructs may be prepared substituting the CH2-CH3 regions of the heavy chain of one specificity of a bispecific antibody by a scFv of a third specificity while the CH2-CH3 regions of the heavy chain of the other specificity are removed, e.g. by introduction of a stop codon (at the end of the "hinge" region) into the coding gene for example by homologous recombination. It is also possible to prepare trispecific scFv constructs. In this case three VH-VL regions representing three different specificities are arranged in series.

According to the invention, there are for example used intact trifunctional bispecific antibodies. Intact bispecific antibodies are a combination of two antibody semi-molecules (each of one H and L immunoglobulin chain) each representing one specificity and, like normal antibodies, having in addition an Fc portion which performs the well known effector functions. Preferably, they are prepared by quadroma technology. This method of preparation is described representatively in DE-A-44 19 399. This document is incorporated by reference in its entirety for the purpose of complete disclosure also with respect to a definition of trifunctional bispecific antibodies.

Methods of producing polyclonal and monoclonal antibodies are known to those of ordinary skill in the art, and many antibodies are available. See, e.g., Coligan, Current Protocols in Immunology Wiley/Greene, N.Y., 1991; and Harlow and Lane, Antibodies: A Laboratory Guide Manual, Cold Spring Harbor Press, NY, 1989; Stites et al., (eds.) Basic and Clinical Immunology (4th ed.) Lange Medical Publications, Los Altos, Calif., and references cited therein; Goding, Monoclonal Antibodies: Principles and Practice (2nd ed.) Academic Press, New York, N.Y. 1986; and Köhler and Milstein, Nature 256: 495-497, 1975. Other suitable techniques for antibody preparation include selection of libraries of recombinant antibodies in phage or similar vectors. See, Huse et al., Science 246: 1275-1281, 1989; and Ward et al., Nature 341: 544-546, 1989. "Specific" monoclonal and polyclonal antibodies and antisera (or antiserum) will usually bind with a KD of at least about 0.1 µM, preferably at least about 0.01 [mu]M or better, and most typically and preferably about 0.001 µM, or better.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faulkner et al, Nature 298:286, 1982; Morrison, J. Immunol. 123:793, 1979; Morrison et al., Ann. Rev. Immunol. 2:239, 1984). Detailed methods for preparation of chimeric (humanized) antibodies can be found in U.S. Pat. No. 5,482, 856. Additional details on humanization and other antibody production and engineering techniques can be found in Borrebaeck (ed.), Antibody Engineering, 2"<d> Edition Freeman and Company, NY, 1995; McCafferty et al., Antibody Engineering, A Practical Approach, IRL at Oxford Press, Oxford, England, 1996, and Paul Antibody Engineering Protocols Humana Press, Towata, N.J., 1995.

Also other methods of preparation may be employed as long as they result in the intact trifunctional bispecific antibodies defined above.

Pharmaceutical Preparations

The pharmaceutical preparation containing one or more of the target antigen and the trifunctional antibodies may be administered orally in any acceptable dosage form such as capsules, tablets, aqueous suspensions, solutions or the like. The preparation may also be administered parenterally. That is via the following routes of administration: subcutaneous, intravenous, intraperitoneal, intramuscular, intra-articular, intra-synovial, intrasternal, intranasal, topical, intrathecal, intrahepatic, intratumoral, intralesional, and intracranial injection or infusion techniques. Generally, the preparations will be provided as an intravenous injection or infusion.

The antibodies and target antigen(s) may be administered alone or preferably with a pharmaceutically acceptable carrier, including acceptable adjuvants, vehicles, and excipients. All of these are familiar for those skilled in the art. Preferred is for instance physiologically acceptable saline.

The effective dosage will depend on a variety of factors and it is well within the purview of a skilled physician to adjust the dosage for a given patient according to various parameters such as body weight, the goal of treatment, the highest tolerated dose, the specific formulation used, the route of administration, the response of the patient and the like.

The trAbs employed according to the present invention are preferably administered in an amount of about 1-about 10 µg, further preferred about 2-about 8 µg, about 3-about 7 µg, or 1 to about 5 µg, each per administration. The optimal amounts may be determined by the skilled artisan by means of experimentation.

The target antigen is applied in an amount of about 0.1 to 500 µg, further optionally in an amount of about 0.1 to 400 µg, about 0.1 to 300 µg, about 0.1 to 200 µg, about 0.1 to 100 µg, about 0.1 to 50 µg, about 0.1 to 10 µg, or about 0.1 to 1 µg.

The number of administrations of the pharmaceutical preparation of the invention can be selected by the physician in accordance with the patient's need, particularly the severity of the disease, the patient's response, the dose applied and other various factors known in the art. Optionally said administration is repeated two or three times.

Said pharmaceutical composition may be in the form of a kit-of-parts wherein said target antigen, said further additional antigens and said antibody are included in at least two spatially distinct containers and are administered separately, or wherein said antibody is contained in a separate container and is administered separately from the target antigen and the one or more further antigens.

The carrier used in the pharmaceutical compositions of the invention may be selected from:
VLPs (e.g. HBV-vaccines: Engerix-B, Twinrix; HPV-vaccines: Gardasil, Cervarix)
chimeric VLPs with covalently linked or associated protein antigens as those described by Michel et al., Vaccine 2007: HIV-1 CTL epitopes inserted in HBV-VLPs (HBsAg); or Reichel et al., Current Nanoscience 2006: Polyoma VLPs with associated/packaged target antigens as antigen delivery vehicles; or Jenning and Bachmann, Biol. Chem. 2008 and *Ann. Rev. Pharmacol. Toxicol.* 2009:

VLPs (e.g. Qβ-bacteriophages) associated with CpG (Toll-like receptor 9 agonist) and/or crosslinked epitopes or antigens for immune intervention The RTS,S malaria vaccine candidate is a recombinant protein that fuses a part of the *P. falciparum* circumsporozoite protein with the hepatitis B virus surface antigen. Combined with a proprietary GSK Adjuvant System, RTS,S induces the production of antibodies and T cells that are believed to diminish the malaria parasite's ability to infect, develop, and survive in the human liver. (GSK-Fact sheet RTSS fact sheet (GSK, press release, 2010)).

single protein antigens

Vantomme et al., J. Immunther. 2004:

MAGE-3 combined with ASO$_2$B adjuvant for therapeutic vaccination of patients with solid metastatic MAGE-3 positive tumors.

multi-antigen polypeptides

Bull et al., PLoSone 2007:

A vaccine comprising a fusion construct designated HAV containing components of two secreted and two cell surface *Mycobacterium avium* subspecies *paratuberculosis* proteins was developed. HAV was transformed into DNA, human Adenovirus 5 (Ad5) and Modified Vaccinia Ankara (MVA) delivery vectors.

heterologous fusion proteins

Olsen et al., Infect. Immun. 2001, 2004; Langermans et al., Vaccine 2005:

The fusion protein antigen Ag85B-ESAT6 of *Mycobacterium tuberculosis* is a highly efficient vaccine against tuberculosis.

It is to be understood that various modifications to the invention will be apparent to and can readily be made by those skilled in the art, given the disclosure herein, without departing from the scope and materials of this invention. The following examples are for purposes of illustration only and are not meant to limit the invention in any way.

Example 1

As single carrier antigen for immunization purposes with trifunctional anti-CD3 triggering antibodies, the human EpCAM protein was selected (Strnad et al., 1989). Based on the publication data described above different covalently linked protein entities or fusion proteins behave as one unit [carrier plus guest antigen(s)] with comparable immunization results. In other words, if in a given immunization experiment EpCAM will be immunogenic in terms of inducing humoral and cell-mediated immune responses then at the same time an antigen of choice conjugated or fused to EpCAM would elicit similar immunological effects. On the molecular and cellular level this similar reactiveness towards different protein species is simply reflected by the aggregate structure originated from covalently linked or associated protein entities that is phagocytozed, processed and presented to T cells via a single APC in context of a certain immunostimulatory environment. In contrast to linked proteins it is more unlikely that single unconjugated proteins are processed and presented by the same APC, thus again may underline the innovative character of this invention. Only the anti-CD3 triggering and activatory Fc-gamma-receptor engagement by means of trifunctional bispecific or trispecific antibodies may create such locally limited stimuli ("immunostimulatory footprint") that makes the entirety of immune responses comparable between 2 different covalently linked or associated proteins in terms of predictability, onset, duration and strength.

Briefly, for studying humoral immune responses evoked against the recombinant human EpCAM protein antigen, three female BALB/c mice per group were subcutaneously (s.c.) immunized as outlined in Table I. In addition, to assess anti-EpCAM antibody titer appropriate blood samples were taken at indicated time points and the anti-EpCAM antibody titers were determined as described herein. Group B only showed markedly enhanced mouse anti-EpCAM antibody titers on day 61 and 105, whereas all other immunization groups generally failed in the induction of anti-EpCAM antibody responses (FIG. 2). This fact is especially important for group D with the identical EpCAM amount as compared to group B settings.

The ELISA method used in the present examples has bee performed as follows.

Following the time schedule, sera from immunized mice were collected and kept at −20° C. For performing mouse anti-EpCAM antibody ELISA, 96-well plates (Greiner, Germany) were coated at 4° C. overnight with 1 μg/ml recombinant EpCAM IMAC in PBS (batch of Nov. 13, 2008, c=1.1 mg/ml). Thereafter, plates were blocked at room temperature for 1 h with 4% BSA in PBS. Each serum samples of each mouse per group were all diluted 1:30 and then 8-fold serially diluted 1/2 in low cross dilution buffer (Candor Bioscience GmbH, Germany). As positive control the anti-EpCAM antibody HO-3 was used (Ruf et al., Br J Cancer 97(3):315, 2007). After 1 h incubation at room temperature the samples were washed three times with Tris/HCl buffer (pH 7.9-8.19). As secondary detection antibodies the following biotinylated antibodies were used in equivalent volumes and diluted to 1:5.000 in low cross dilution buffer: (i) rat anti-mouse IgG2a (ATCC no. HB-90), (ii) rat anti-mouse IgG1/IgG2a/IgG2b/IgG3 (ATCC no. HB-128) and (iii) rat anti-mouse IgG1 (obtained from Dr. E. Kremmer, Helmholtz-Zentrum Munich, Germany). Subsequently, after 1 h incubation at room temperature, plates were washed three times again with Tris/HCl buffer (pH 7.9-8.1), and the streptavidin/β-galactosidase conjugate (purchased from Roche Diagnostics, Germany) diluted at 1:2.500 in low cross dilution buffer was added to the samples. After 30-60 min incubation and three subsequent washing steps with Tris/HCl buffer (pH 7.9-8.1) the OD was determined at 570 nm (OD570) with a VersaMax ELISA reader (Molecular Devices, USA).

TABLE I

Immunization schedule towards adjuvant-like effects of trifunctional antibodies (exp. 1)

| Group (n) | Immunization Schedule | Blood Samples |
|---|---|---|
| A (3) | 0.4 μg BiLu[1] + 0.1 μg EpCAM[2]/ 100 μl PBS s.c. on day 0, 21, 49 and 98 | 50 μl (1 aliquot, −80° C.) on day 7, 28, 61 and 105 |
| B (3) | 2 μg BiLu + 0.5 μg EpCAM/ 100 μl PBS s.c. on day 0, 21, 49 and 98 | 50 μl (1 aliquot, −80° C.) on day 7, 28, 61 and 105 |

TABLE I-continued

Immunization schedule towards adjuvant-like effects of trifunctional antibodies (exp. 1)

| Group (n) | Immunization Schedule | Blood Samples |
|---|---|---|
| C (3) | 0.1 μg EpCAM/100 μl PBS s.c. on day 0, 21, 49 and 98 | 50 μl (1 aliquot, −80° C.) on day 7, 28, 61 and 105 |
| D (3) | 0.5 μg EpCAM/100 μl PBS s.c. on day 0, 21, 49 and 98 | 50 μl (1 aliquot, −80° C.) on day 7, 28, 61 and 105 |

[1]BiLu: Batch KA 150208 (anti-human EpCAM × anti-murine CD3);
[2]recombinant human EpCAM (batch: EpCAM IMAC of Nov. 13, 2008; 1.1 mg/ml). Abbreviation: s.c., subcutaneously.

Example 2

Briefly, for studying humoral immune responses evoked against the recombinant human EpCAM protein antigen in a comparative analysis (trifunctional anti-EpCAM×anti-CD3 antibody BiLu vs. Alhydrogel, a standard adjuvant), 10 female BALB/c mice per group were s.c. immunized as outlined in Table II. Of note, Alhydrogel purchase from Sigma is a sterilized aluminium hydroxide wet gel suspension which has been tested free of pyrogenicity. To assess mouse anti-EpCAM antibody titer, appropriate blood samples were taken at indicated time points and the mouse anti-EpCAM antibody titers were determined as described previously in the Methods chapter.

TABLE II

Immunization schedule towards adjuvant-like effects of trifunctional antibodies (exp. 2)

| Group (number of mice) | Immunization Schedule | Blood Samples |
|---|---|---|
| A (n = 10) | 0.5 μg EpCAM/200 μl PBS s.c. on day 0, 7, 28, 56 | 100 μl (2 Aliquots, −80° C.) on day 5, 26, 54, 68 |
| B (n = 10) | 0.5 μg EpCAM + 2 μg BiLu[1]/200 μl PBS s.c. on day 0, 7, 28, 56 | 100 μl (2 Aliquots, −80° C.) on day 5, 26, 54, 68 |
| C (n = 10) | 0.5 μg EpCAM + 20 μl [3]Alhydrogel/200 μl PBS s.c. an Tag 0, 7, 28, 56 | 100 μl (2 Aliquots, −80° C.) on day 5, 26, 54, 68 |
| D (n = 10) | 2 μg BiLu/200 μl PBS s.c. on day 0, 7, 28, 56 | 100 μl (2 Aliquots, −80° C.) on day 5, 26, 54, 68 |

[1]BiLu: Batch KA 150208 (anti-human EpCAM × anti-murine CD3);
[2]recombinant human EpCAM (batch: EpCAM IMAC of Nov. 13, 2008; 1.1 mg/ml);
[3]Alhydrogel (Sigma, A8222-250 ml; stored at −80° C.);. Abbreviation: s.c., subcutaneously.

To assess the respective EpCAM-specific antibody titers, appropriate blood samples were taken at indicated time points and the antibody titers were determined by means of ELISA read-out as described briefly in the Methods chapter. The immunization results in terms of humoral anti-EpCAM immune responses (median of antibody titers presented in Table Ill.) can be summarized as follows:

Only the immunization group B showed markedly enhanced mouse anti-EpCAM antibody titers on day 54 and 68, whereas the immunization groups A and D generally failed in the induction of anti-EpCAM antibody responses (Table III). Interestingly, the immunization schedule with the standard antigen formulation, recombinant EpCAM plus adjuvant Alhydrogel (group C), performed at identical EpCAM antigen doses to group B, led only to low mouse anti-EpCAM antibody titers at day 68 post immunization. Thus, the trifunctional antibody formulation (i.e. anti-Ep-CAM×anti-CD3, BiLu) together with the targeted antigen (EpCAM) is far superior to standard antigen formulations at equivalent doses using for example Alhydrogel (aluminum salt) as adjuvant.

TABLE III

Mouse anti-EpCAM antibody titers induced by different recombinant EpCAM formulations including anti-EpCAM × anti-CD3 antibody BiLu or Alhydrogel

| Group (number of mice) | Immunization Schedule | Mouse anti-EpCAM titers (median) |
|---|---|---|
| A (n = 10) | 0.5 μg EpCAM/200 μl PBS s.c. on day 0, 7, 28, 56 | Day 5: 30<br>Day 26: 30<br>Day 54: 30<br>Day 68: 30 |
| B (n = 10) | 0.5 μg EpCAM + 2 μg BiLu[1]/200 μl PBS s.c. on day 0, 7, 28, 56 | Day 5: 30<br>Day 26: 90<br>Day 54: 15.360<br>Day 68: 61.440 |
| C (n = 10) | 0.5 μg EpCAM + 20 μl [3]Alhydrogel/200 μl PBS s.c. an Tag 0, 7, 28, 56 | Day 5: 30<br>Day 26: 30<br>Day 54: 30<br>Day 68: 300 |
| D (n = 10) | 2 μg BiLu/200 μl PBS s.c. on day 0, 7, 28, 56 | Day 5: 30<br>Day 26: 30<br>Day 54: 30<br>Day 68: 30 |

[1]BiLu: Batch KA 150208 (anti-human EpCAM × anti-murine CD3);
[2]recombinant human EpCAM (batch: EpCAM IMAC of Nov. 13, 2008; 1.1 mg/ml);
[3]Alhydrogel (Sigma, A8222-250 ml; stored at −80° C.);. Abbreviation: s.c., subcutaneously.

Example 3

Figure 3:
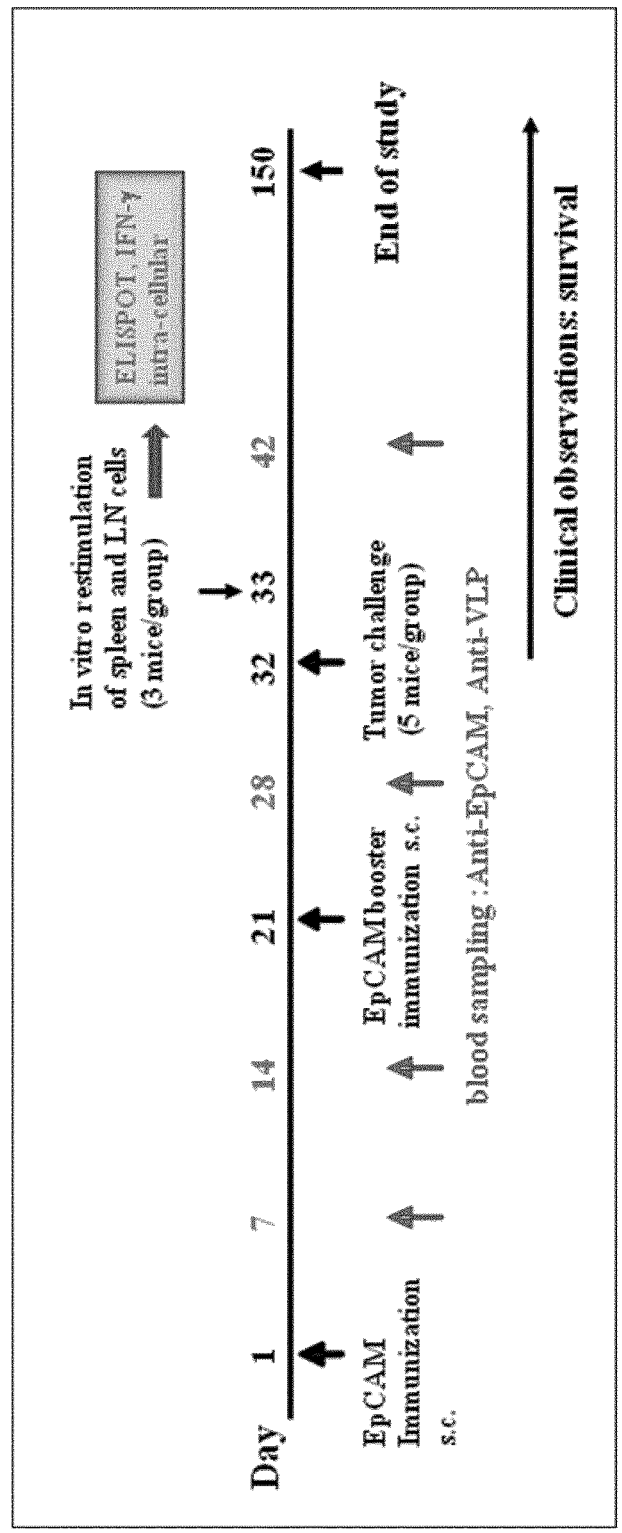
FIG. 3: Study design of Example 3

To assess besides humoral also cell-mediated immune responses the following experimental study was performed in mice. For the comparative analysis of different immunization mixtures eight female BALB/c mice per group were s.c. immunized against the EpCAM protein and blood samples were drawn as outlined in Table IV and FIG. 3. On day 32 the experimental groups were separated: Five mice per group were challenged with EpCAM transfected CT26 tumor cells to evaluate immunization induced tumor protection in vivo. The residual three animals per group were sacrificed on day 33 for spleen and lymph node cell preparations to analyze EpCAM-specific cellular immune responses in vitro.

TABLE IV

Immunization schedule to induce adjuvant-like effects of trispecific antibodies (ex. 3)

| Group (n) | Immunization Schedule | Blood Samples |
|---|---|---|
| A (8) | 0.5 μg EpCAM[2]/200 μl PBS s.c. on days 0 and 21 | 100 μl (1 aliquot, −80° C.) on days 7, 14, 28, and 42 |
| B (8) | 0.5 μg EpCAM[2] + 2 μg BiLu[1]/200 μl PBS s.c. on days 0 and 21 | 100 μl (1 aliquot, −80° C.) on days 7, 14, 28, and 42 |
| C (8) | 0.5 μg VLP-EpCAM[3]/200 μl PBS s.c. on days 0 and 21 | 100 μl (1 aliquot, −80° C.) on days 7, 14, 28, and 42 |
| D (8) | 0.5 μg VLP-EpCAM[3] + 2 μg BiLu[1]/200 μl PBS s.c. on days 0 and 21 | 100 μl (1 aliquot, −80° C.) on days 7, 14, 28, and 42 |

TABLE IV-continued

Immunization schedule to induce adjuvant-like
effects of trispecific antibodies (ex. 3)

| Group (n) | Immunization Schedule | Blood Samples |
|---|---|---|
| E (8) | 0.5 μg VLP[4] + 2 μg BiLu/ 200 μl PBS s.c. on days 0 and 21 | 100 μl (2 aliquots, −80° C.) on day 12, 26, 54, and 68 |

[1]anti-human EpCAM × anti-murine CD3 BiLu: Batch KA 150208;
[2]recombinant human EpCAM (Batch: EpCAM IMAC of Nov. 13, 2008; 1.1 mg/ml);
[3]EpCAM protein conjugated to virus-like-particles (VLP, TRION Research, batch 12.08.11, aliquoted and stored in 50% glycerol at −20° C.);
[4]virus-like-particles from murine polyoma virus VP1 protein (Vilnius University, Institute of Biotechnology, Vilnius, Lithuania, aliquot and stored in 50% glycerol at −20° C.) (Abbing et al., Virology 279: 27410, 2004; Gedivilaite et al., Virology 354: 252, 2006)

1. Assessment of Humoral Immune Responses

To assess EpCAM- and VLP-specific antibody titers appropriate blood samples were taken at indicated time points and the appropriate antibody titers were determined by means of ELISA. Anti-EpCAM titers were measured as described in example I. For the determination of anti-VLP titers the ELISA was modified by coating 1 μg/ml of recombinant VLP instead of recombinant EpCAM protein. As a positive control 1 μg/ml murine anti-VP1 specific antibody (Abcam, # Ab34755) was used.

The immunization results in terms of humoral immune responses can be summarized as follows (Table V):

I. Anti-EpCAM Response:

The highest titers were observed in group B which started on day 28 and peaked on day 42, 10 days after the challenge with EpCAM-transfected CT26 tumor cells. Intermediate titers were measured for groups C and D, lowest titers for groups A and E. Thus, the trifunctional antibody formulation together with soluble EpCAM antigen (group B) was most efficient in the generation of a humoral immune response.

II. Anti-VLP Response:

VLP-specific antibodies could be detected in all groups that were immunized with VLP preparations. The humoral immune response started early on day 7, further increased on day 14, and finally peaked on day 28, one week after the s.c. booster immunization. High antibody titers were induced by both VLP and by VLP-EpCAM conjugate preparations. Interestingly, the addition of the BiLu antibody significantly increased titer production 5-8 times in median on days 14 and 28, respectively. Thus, the trifunctional antibody BiLu not only fostered antibody production against the targeted antigen EpCAM, but also against the conjugated VLP proteins.

TABLE V

Mouse anti-EpCAM/VLP antibody titers induced by
different recombinant EpCAM formulations including
anti-EpCAM × anti-CD3 antibody BiLu and VLP

| Group (number of mice) | Immunization Schedule | Anti-EpCAM titers (median) | Anti-VLP titers (median) |
|---|---|---|---|
| A (8: days 7, 14, 28 5: day 42) | 0.5 μg EpCAM[2]/ 200 μl PBS s.c. on days 0 and 21 | Day 14: 30 Day 28: 30 Day 42: 480 | — |
| B (8: days 7, 14, 28 5: day 42) | 0.5 μg EpCAM[2] + 2 μg BiLu[1]/200 μl PBS s.c. on days 0 and 21 | Day 14: 30 Day 28: 45 Day 42: 61.440 | — |
| C (8: days 7, 14, 28 5: day 42) | 0.5 μg VLP-EpCAM[3]/200 μl PBS s.c. on days 0 and 21 | Day 14: 30 Day 28: 30 Day 42: 3.840 | Day 7: 60 Day 14: 11.520 Day 28: 184.320 |
| D (8: days 7, 14, 28 5: day 42) | 0.5 μg VLP-EpCAM[3] + 2 μg BiLu[1]/200 μl PBS s.c. on days 0 and 21 | Day 14: 30 Day 28: 30 Day 42: 7.680 | Day 7: 90 Day 14: 61.440 Day 28: 1.474.560 |
| E (8: days 7, 14, 28 5: day 42) | 0.5 μg VLP[4] + 2 μg BiLu/200 μl PBS s.c. on days 0 and 21 | Day 14: 30 Day 28: 30 Day 42: 120 | — |

2. Assessment of Cellular Immune Responses

For the analysis of EpCAM-specific cellular immune responses 3 mice per group were sacrificed on day 33, 11 days after the s.c. booster immunization. As an additional control non-immunized, naïve mice were included: Spleen and inguinal and mesenterial lymph node (LN) cells were prepared and re-stimulated for 7 days either with 1 μg/ml recombinant EpCAM protein (TRION Research, Batch: EpCAM IMAC of Nov. 13, 2008; 1.1 mg/ml) or with 10 μg/ml of the EpCAM-derived peptide 225 (metabion, amino acid sequence: LFH SKK MDL). Therefore, $7.5 \times 10^6$ irradiated (30 Gy) spleen cells from a naïve donor Balb/c mouse were used as antigen presenting cells (APC) and loaded over night with the EpCAM protein. Thereafter, $7.5 \times 10^6$ cells from cell preparations of immunized mice were added. Alternatively, APC were loaded with the EpCAM peptide 225 one hour before the addition of the cell preparations. All approaches were performed in 24 well plates with $15 \times 10^6$ cells per well, suspended in re-stimulation medium composed of RPMI medium supplemented with 10% fetal calf serum, 10 mM HEPES buffer, 2 mM L-glutamine, 1× penicillin/streptomycin, 50 μM β-mercapto-ethanol, and 60 unites/ml recombinant mouse IL-2 (Miltenyi Biotech, #130-094-055). Cells were then incubated at 37° C. and 5% $CO_2$ for 7 days and finally collected from the wells, washed once with medium described above, counted and used for intracellular IFN-g staining and IFN-g ELISPOT assays.

For the intracellular IFN-g staining $10^6$ cells/96 well were incubated for 4 hours in re-stimulation medium supplemented with 1 μg/ml PMA, 1 μg/ml ionomycin, and 1× brefeldin A (200 μl final volume) for the stimulation and accumulation of intracellular IFN-g. Then, cells were washed and surface-stained with FITC or PE-conjugated anti-mouse CD3, CD4 and CD8 antibodies (Becton Dickinson), washed and fixed with IC fixation buffer (eBioscience, #00-8222-49), washed again and treated two times with permeabilization buffer (eBioscience, #00-8333-56). Cells were then stained intracellular with APC-conjugated anti-mouse IFN-g antibody (Biozol Diagnostic, # BLD-505810) or APC-conjugated rat IgG1/kappa isotype control (Biozol Diagnostic, # BLD-400412), washed and re-suspended in FACS buffer (PBS, 0.1% FCS). $10^6$ cells per sample were stained and measured using a FACSCalibur (Becton Dickinson) flow cytometer.

For the IFN-g ELISPOT assay cells re-stimulated with EpCAM protein or EpCAM-peptide 225 were transferred on a 96 well IFN-g ELISPOT plate (Becton Dickinson, ELISPOT mouse IFN-g Kit #552569) and incubated for 20-22 hours at 37° C. and 5% $CO_2$. 100.000 cells per well were analyzed and each sample was measured in quadruplicates. ELISPOT plates were developed according to the manufacturers recommendations. IFN-g spot acquisition was performed by CTL Europe GmbH applying Immuno-Spot software 5.0.40.

Figure 4:
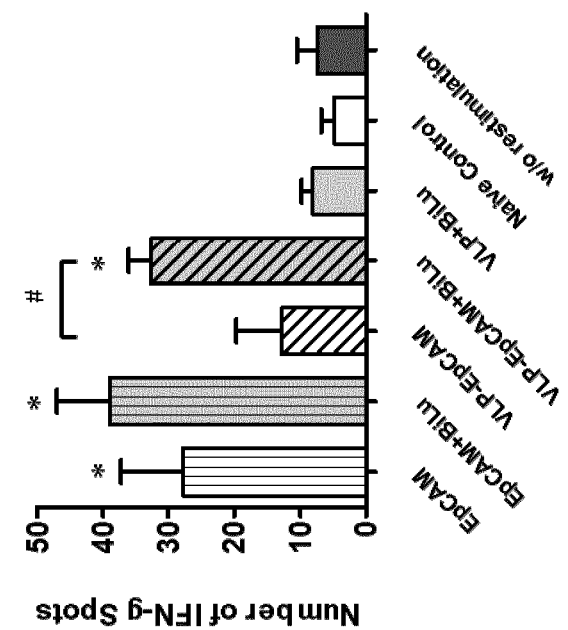
FIG. 4: IFN-g ELISPOT outcome of immune cells re-stimulated with EpCAM protein Bars represent mean values of quadruplicate determinations with SD (error bars). Asterisks indicate statistically significant difference of spot numbers in comparison to naive control (two-tailed, unpaired t-test, p<0.05). In addition, the # symbol indicates the statistically significant difference between both sets of data (two-tailed, unpaired t-test, p=0.0023). A cell pool of each three mice per immunization group was analyzed.

As shown in FIG. 4 there was a significant increase in IFN-g spot production in mice immunized with EpCAM (group A), EpCAM+BiLu (group B), or VLP-EpCAM+BiLu (group D) in comparison to the naïve control mice. Mean spot values increased from 4.75 (control) to 27.75 (A), to 39 (B), and to 32.5 (D). Of note, the difference between group C (VLP-EpCAM) and D (VLP-EpCAM+BiLu) was also statistically significant (12.75 versus 32.5, two-tailed, unpaired t-test, p=0.0023). This demonstrates that the addition of the trifunctional antibody BiLu to the VLP-EpCAM antigen preparation significantly augmented the induced cellular immune response against the EpCAM antigen as measured by IFN-g ELISPOT.

Figure 5:
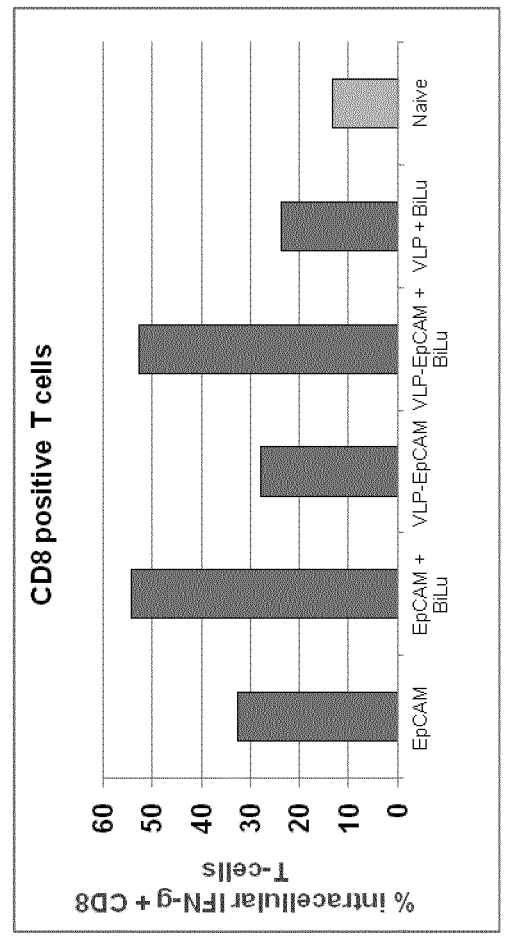
FIG. 5A: IFN-g production (intracellular) of CD8 positive T cells restimulated with EpCAM protein
FIG. 5B: IFN-g production (intracellular) of CD4 positive T cells restimulated with EpCAM protein
Figure 5:
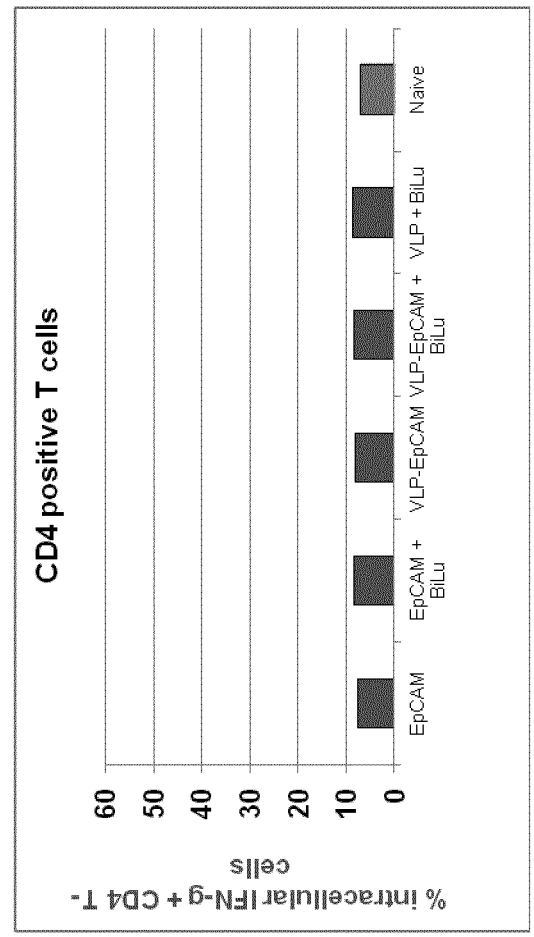

As shown by the intracellular FACS analysis (FIG. 5 A+B) mainly CD8 positive T cells produced IFN-g, whereas CD4 positive T cells contributed to a much lesser extent. This indicates that cytotoxic T lymphocytes (CTL) directed against the EpCAM protein were generated and that their numbers increased in mice vaccinated with the trifunctional antibody BiLu in combination with the EpCAM protein. In order to evaluate the exact antigen specificity of the CTL response an IFN-g ELISPOT assay was performed with immune cells re-stimulated with the EpCAM-derived peptide 225. This nonamer peptide with the amino acid sequence LFH SKK MDL was chosen as a putative human EpCAM-specific CTL epitope for murine MHC class I-binding. A search analysis with an epitope prediction software (http://www.syfpeithi.de/Scripts/MHCServer.dll/EpitopePrediction.htm) resulted in a good binding score of 20 for the binding of the peptide 225 to the MHC class I haplotype $H2-K^d$. Importantly, the peptide sequence differs in four amino acids (44%) from the homologue mouse EpCAM peptide. Thus, peptide 225 should be recognized as foreign by the mouse immune system preventing tolerance induction.

Figure 6:
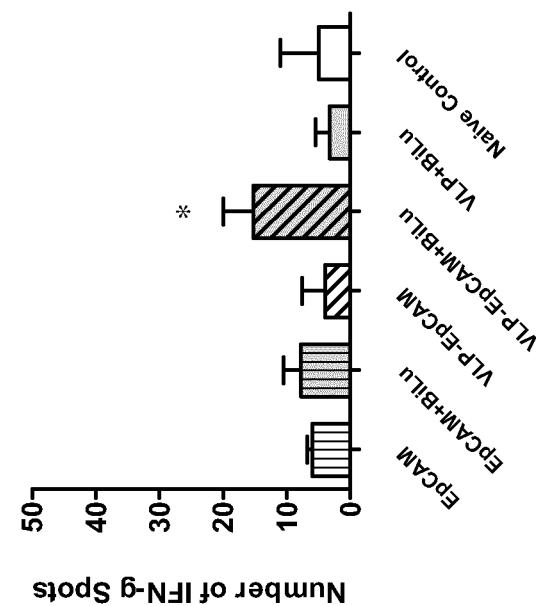
FIG. 6: IFN-g ELISPOT outcome of immune cells re-stimulated with EpCAM-derived peptide 225

Indeed, as shown in FIG. 6 a significant increase of IFN-g production was measured for the immunization group D receiving VLP-EpCAM plus BiLu antibody. The mean number of spots in comparison to the control group C (VLP-EpCAM w/o BiLu) and the naïve control was 15.25 versus 4, respectively 5 (two-tailed unpaired t-test, p=0.0089). This demonstrates that the use of the BiLu antibody in combination with VLP-EpCAM conjugates fostered the development of CTL specific for the EpCAM-derived peptide 225.

3. Assessment of Tumor Protection In Vivo

To evaluate whether induced humoral and cellular immune responses led to tumor protection against human EpCAM expressing CT26 mouse adenocarcinoma cells (CT26-EpCAM) five mice per immunization group were challenged intraperitoneally (i.p.) on day 32 with a lethal dose of $5 \times 10^5$ tumor cells. As depicted in FIG. 7A-C mice which received the BiLu antibody in addition to the EpCAM protein vaccine preparation had a significant prolonged survival in comparison to the respective control groups without BiLu antibody. In both immunization settings either with the soluble EpCAM protein or with the VLP-conjugated EpCAM protein the addition of the trifunctional antibody BiLu resulted in increased protection against the EpCAM expressing tumor cells. Of note, the survival of mice directly correlated with the results of the IFN-g specific ELISPOT assay for monitoring MHC class I-restricted EpCAM-specific CD8 T cells (FIG. 4). These results underline the outstanding importance of cell-mediated immune responses for tumor defense.

4. Conclusions

The experimental findings of Example 3 clearly support the prominent adjuvant capability of trifunctional antibodies in terms of induction of humoral and cell-mediated immunity. Taken together, soluble EpCAM or EpCAM conjugated to VLPs and targeted by the trifunctional anti-EpCAM×anti-murine CD3 antibody BiLu to T lymphocytes and accessory cells (like dendritic cells, macrophages/monocytes or B lymphocytes) lead to (i) more than 120-fold increase of anti-EpCAM titer (Table V) compared to the control group w/o trAb BiLu, (ii) more than 6-fold increase of anti-VLP antibodies (Table V) compared to the control group w/o trAb BiLu (only 2-fold increase of anti-EpCAM antibody titers due to the lower surface density of EpCAM on VLPs), (iii) EpCAM-specific increase of IFN-gamma-secreting T cells (i.e. predominantly $CD8^+$ T cells) restimulated with recombinant EpCAM-protein in comparison with the control w/o trAb BiLu (FIG. 4 and FIG. 5A), (iv) significantly increase of EpCAM-specific IFN-gamma-secreting T cells (i.e. predominantly $CD8^+$ T cells) of VLP-EpCAM/BiLu-immunized mice restimulated with a MHC-class-I-restricted EpCAM-peptide in comparison with the control w/o trAb BiLu (FIG. 6), (v) significant differences in survival between EpCAM/BiLu-immunized mice and the control group w/o trAb or between VLP-EpCAM/BiLu-immunized mice and the control group w/o trAb BiLu upon CT26-EpCAM tumor challenge (FIGS. 7A and 7B)

It should be stressed that the EpCAM-concentration of the VLP-EpCAM conjugate applied for mice immunization was considerably reduced by approximately 70% as compared to the vaccine formulation with recombinant EpCAM protein alone. Of note, the EpCAM/BiLu or the VLP-EpCAM/BiLu vaccine formulation appeared to predominantly stimulate $CD8^+$ T cells by using alternate MHC-class-I antigen processing/presentation pathways (FIG. 4 and FIG. 5A), that were different from antigen trafficking routes of soluble external proteins within antigen presenting cells. Usually, these external proteins were predominantly presented by MHC-class-II-molecules to $CD4^+$ T cells which were not stimulated by all vaccine formulations used, especially not by the VLP-EpCAM/BiLu or EpCAM/BiLu compounds having adjuvant potential.

However, the lack of $CD4^+$ T cell stimulation evoked by the EpCAM or VLP-EpCAM control immunizations could be best explained by the low EpCAM antigen amount used for animal vaccination in the absence of an appropriate adjuvant. Most importantly, the in vitro restimulation of splenocytes from EpCAM/BiLu- or VLP-EpCAM/BiLu-immunized mice with recombinant EpCAM protein prevalently triggered $CD8^+$ T cells.

REFERENCES

Dietrich, J., C. Aagaard, R. Leah, A. W. Olsen, A. Stryhn, T. M. Doherty, and P. Andersen. 2005. Exchanging ESAT6 with TB10.4 in an Ag85B fusion molecule-based tuberculosis subunit vaccine: efficient protection and ESAT6-based sensitive monitoring of vaccine efficacy. *J. Immunol.* 174: 6332.

Garcea, R. L., and L. Gissmann. 2004. Virus-like-particles as vaccines and vessels for the delivery of small molecules. *Curr. Opin. Biotechnol.* 15: 513.

Glenn and O'Hagan. 2007. Adjuvants: progress, regress and pandemic preparedness. *Expert Rev. Vaccines* 6(5): 651.

Jennings, G. T., and M. F. Bachmann. 2009. Immunodrugs: therapeutic VLP-based vaccines for chronic diseases. *Annu. Rev. Pharmacol. Toxicol.* 49: 303.

Jennings, G. T., and M. F. Bachmann. 2008. The coming of age of virus-like particle vaccines. *Biol. Chem.* 389: 521.

Langermans, J. A., T. M. Doherty, R. A. Vervenne, T. Laan, K. Lyashchenko, R. Greenwald, E. M. Agger, C. Aagaard, H. Weiler, D. Soolingen, et al. 2005. Protection of macaques against *Mycobacterium tuberculosis* infection by a subunit vaccine based on a fusion protein of antigen 85B and ESAT-6. *Vaccine* 23: 2740.

Michel M, Y. C. Lone, M. Centlivre, P. Roux, S. Wain-Hobson, and M. Sala. 2007. Optimisation of secretion of recombinant HBsAg virus-like particles: Impact on the development of HIV-1/HBV bivalent vaccines. *Vaccine* 25: 1901.

Olsen, A. W., A. Williams, L. M. Okkels, G. Hatch, and P. Andersen. 2004. Protective effect of a tuberculosis subunit vaccine based on a fusion of antigen 85B and ESAT-6 in the aerosol guinea pig model. *Infect. Immun.* 72: 6148.

Olsen, A. W., L. A. van Pinxteren, L. M. Okkels, P. B. Rasmussen, and P. Andersen. 2001. Protection of mice with a tuberculosis subunit vaccine based on a fusion protein of antigen 85b and esat-6. *Infect. Immun.* 69: 2773.

Reichel, C., Brinkman, M., Ruehland, C., Reiser, C. O. A. and J. Hess. 2006. Heterologous virus-like-particles: recombinant nanosystems as versatile antigen delivery devices for immune intervention. *Current Nanoscience* 2: 295.

Ruf, P., and H. Lindhofer. 2001. Induction of along-lasting antitumor immunity by a trifunctional bispecific antibody. *Blood* 98:2526.

Snider, D. P., A. Kaubisch, and D. M. Segal. 1990. Enhanced antigen immunogenicity induced by bispecific antibodies. *J. Exp. Med.* 171: 1957.

Strnad, J., Hamilton A. E., Beavers L. S., Gamboa G. C., Apelgren L. D., Taber L. D., Sportsman J. R., Bumol T. F., Sharp J. D., R. A. Gadski. 1989. Molecular cloning and characterization of a human adenocarcinoma/epithelial cell surface antigen complementary DNA. *Cancer Res.* 49:314.

Tissot, A. C., R. Renhofa, N. Schmitz, J. Cielens, and E. Meijerink, et al. 2010. Versatile virus-like particle carrier for epitope based vaccines. *PLoS ONE* 5: e9809.

The invention claimed is:

1. A pharmaceutical composition comprising:
   1) a trifunctional bispecific antibody and/or a trispecific antibody having the following properties:
      (a) binding to a T cell via CD3 and activating said T cell;
      (b) binding to a target antigen other than CD3;
      (c) binding to Fcγ-receptor type I, II and/or III positive cells via an Fc-portion, or by a third antigen specificity; and
   2) a pharmaceutically acceptable carrier selected from the group consisting of homologous virus-like particles (VLP) and heterologous/chimeric VLP, wherein said target antigen and optionally one or more further antigens are associated with or conjugated to the VLP.

2. The pharmaceutical composition according to claim 1 wherein said target antigen is carrier-specific but not disease-associated and wherein one or more further antigens are disease-associated and conjugated to or associated with the VLP.

3. The pharmaceutical composition according to claim 1, wherein said target antigen is a disease-specific target antigen selected from the group consisting of antigens specific for tumors, viruses, bacteria, fungi, and protozoa, or an immunologically active epitope thereof.

4. The pharmaceutical composition according to claim 1, wherein said target antigen is a carrier protein or an immunologically active epitope thereof.

5. The pharmaceutical composition according to claim 1, wherein said composition is in the form of a vaccine formulation.

6. The pharmaceutical composition according to claim 1 wherein said one or more further antigens are conjugated to or associated with the VLP.

7. The pharmaceutical composition according to claim 6 wherein the target antigen is displayed by the VLP.

8. The pharmaceutical composition according to claim 1 wherein said target antigen is a non-disease associated antigen conjugated to or associated with one or more disease-associated antigens.

9. The pharmaceutical composition according to claim 1, wherein said carrier has a medium diameter of about 10-500 nm, and/or wherein said trifunctional bispecific and/or trispecific antibody is contained in an amount of about 1-10 μg, and/or wherein said target antigen is contained in an amount of about 0.1-500 μg.

10. A kit comprising two containers, the first container containing a trifunctional bispecific and/or trispecific antibody having the following properties:
    (a) binding to a T cell via CD3 and activating said T cell;
    (b) binding to a target antigen other than CD3;
    (c) binding to Fcγ-receptor type I, II and/or III positive cells via an Fc-portion, or by a third antigen specificity; and
    a second container containing a carrier selected from the group consisting of homologous virus-like particles (VLP) and heterologous/chimeric VLP, wherein said target antigen and optionally one or more further antigens are conjugated to or associated with the VLP.

11. A kit according to claim 10 wherein said target antigen is carrier-specific but not disease-associated, and wherein one or more further antigens are disease-associated and conjugated to or associated with the VLP.

12. A method for immunizing a mammal subject, comprising administering to said subject a pharmaceutically effective amount of the pharmaceutical composition of claim 1 to evoke a cell-mediated or a humoral immune response or a combination thereof against said target antigen and said optionally one or more further antigens to immunize said mammal subject against said target antigen and said optionally one or more further antigens.

13. The method according to claim 12, wherein said target antigen is a disease-specific target antigen selected from the group consisting of antigens specific for tumors, viruses, bacteria, fungi, and protozoa, or an immunologically active epitope thereof.

14. The method according to claim 12, wherein said target antigen is a carrier protein or an immunologically active epitope thereof.

15. The method according to claim 12, wherein said one or more further antigens are conjugated to or associated with the VLP.

16. The method according to claim 15, wherein said target antigen is displayed by the VLP.

17. The method according to claim 12, wherein said trifunctional antibody is a rat/mouse bispecific antibody.

18. The method according to claim 12, wherein said trifunctional bispecific antibody is selected from at least one member of the following group of isotype combinations in its Fc-region:
rat-IgG2b/mouse-IgG2a,
rat-IgG2b/mouse-IgG2b,
rat-IgG2b/human-IgG1, and
human-IgG1/human-IgG1-[hinge]-human-IgG3*-[CH2-CH3],
wherein * denotes Caucasian allotypes G3m (b+g) with no binding to protein A.

19. The method according to claim 12, wherein said trifunctional bispecific antibody is an anti-target antigen× anti-CD3 antibody having the isotype combination of rat-IgG2b/mouse-IgG2a.

20. The method according to claim 12, wherein said trifunctional bispecific or trispecific antibodies are administered in an amount of about 1-10 µg, optionally wherein said administration is repeated two or three times.

21. The method according to claim 12, wherein said target antigen is administered in an amount of about 0.1-500 µg.

22. The method according to claim 12, wherein said target antigen is a disease-associated antigen selected from the group consisting of tumor-associated antigens, fungal antigens, viral antigens, protozoan and bacterial antigens.

23. The method according to claim 12, wherein said target antigen is carrier-specific but not disease-associated, and wherein one or more further antigens are disease-associated and conjugated to or associated with the VLP.

* * * * *